(12) United States Patent
Dong

(10) Patent No.: US 12,734,339 B2
(45) Date of Patent: Sep. 15, 2026

(54) VENOUS CATHETER DEVICE CAPABLE OF BEING SEALED

(71) Applicant: Zhejiang Baihuo Health Technology Co., Ltd., Shaoxing (CN)

(72) Inventor: Dongsheng Dong, Beijing (CN)

(73) Assignee: Zhejiang Baihuo Health Technology Co., Ltd., Shaoxing (CN)

( * ) Notice: Subject to any disclaimer, the term of this patent is extended or adjusted under 35 U.S.C. 154(b) by 1434 days.

(21) Appl. No.: 17/310,207

(22) PCT Filed: Nov. 25, 2019

(86) PCT No.: PCT/CN2019/120695

§ 371 (c)(1),
(2) Date: Jul. 26, 2021

(87) PCT Pub. No.: WO2020/151359

PCT Pub. Date: Jul. 30, 2020

(65) Prior Publication Data

US 2022/0168548 A1 Jun. 2, 2022

(30) Foreign Application Priority Data

Jan. 27, 2019 (CN) ......................... 201910076864.4

(51) Int. Cl.
*A61M 25/06* (2006.01)
*A61M 25/00* (2006.01)
(Continued)

(52) U.S. Cl.
CPC .... *A61M 25/0662* (2013.01); *A61M 25/0043* (2013.01); *A61M 25/0102* (2013.01);
(Continued)

(58) Field of Classification Search
CPC .............. A61M 25/01; A61M 25/0662; A61M 25/0043; A61M 25/0102;
(Continued)

(56) References Cited

U.S. PATENT DOCUMENTS 5,409,463 A * 4/1995 Thomas ............ A61M 25/0662
604/167.04
5,503,263 A * 4/1996 Watanabe .............. B65H 51/10
198/363
(Continued)

FOREIGN PATENT DOCUMENTS

CN 108578825 A * 9/2018 ........ A61M 25/0017
CN 108939206 A * 12/2018

*Primary Examiner* — Bhisma Mehta
*Assistant Examiner* — Mark A Igel
(74) *Attorney, Agent, or Firm* — Wang Law Firm, Inc.

(57) ABSTRACT

An occludable venous catheter device includes a needle tube with a needle tube base; a venous catheter with a venous catheter base; a sealer, a front portion disposed inside a venous catheter lumen, a front end exposed out of a front-end opening; an occluding wire; an isolating element; a guide passage with a straight tube portion; a front-end opening connected to the venous catheter lumen; wherein the occluding wire is capable of entering the venous catheter lumen; the straight tube portion is coaxial with the venous catheter or is capable of moving in an externally-isolated manner to a position such that a central axis of the straight tube portion coincides with a central axis of the venous catheter; the occluding wire and the guide passage reach directly inside a chamber and are isolated from the outer environment.

3 Claims, 32 Drawing Sheets

(51) Int. Cl.
*A61M 25/01* (2006.01)
*A61M 25/09* (2006.01)

(52) U.S. Cl.
CPC ............... *A61M 2025/0004* (2013.01); *A61M 2025/0681* (2013.01); *A61M 2025/091* (2013.01); *A61M 2205/3368* (2013.01); *A61M 2205/36* (2013.01)

(58) Field of Classification Search
CPC .... A61M 2025/004; A61M 2025/0681; A61M 2025/091; A61M 2025/3368; A61M 2025/36
See application file for complete search history.

(56) References Cited

U.S. PATENT DOCUMENTS 6,264,630 B1 * 7/2001 Mickley ............ A61M 25/1006 604/524
2005/0125002 A1 * 6/2005 Baran ............... A61M 25/0105 604/528
2005/0159728 A1 * 7/2005 Armour ............ A61M 25/0662 604/528
2007/0156084 A1 * 7/2007 Belhe ............... A61B 17/00491 604/57
2010/0004730 A1 * 1/2010 Benjamin ......... A61M 25/0662 604/167.03
2012/0226341 A1 * 9/2012 Schreck .................. A61F 2/954 623/1.11
2013/0274784 A1 * 10/2013 Lenker ............... A61B 17/3417 606/185
2015/0157843 A1 * 6/2015 Pepin ................ A61M 39/0606 604/167.04
2016/0045715 A1 * 2/2016 Galgano ........... A61M 25/0662 604/510
2020/0001051 A1 * 1/2020 Huang .................. A61M 25/06
2022/0087713 A1 * 3/2022 Kim ................... A61B 17/3423
2025/0152918 A1 * 5/2025 Abitabilo .......... A61M 25/0108

* cited by examiner

1
L1
401
L2
40
25a
2331
2303
311
25a
20
402
L3
3
230
25b
L0
16

20
23
233
40
3
230
25b
253
25a
256
25

23
401
250
40
311
240
24
25b
235
25a
25
402
3

20
L1
23
L3
2331
25
L2
40
255

VENOUS CATHETER DEVICE CAPABLE OF BEING SEALED

CROSS-REFERENCE TO RELATED APPLICATIONS

This application is a national stage entry of PCT/CN2019/120695, filed on Nov. 25, 2019, and claims the benefit of priority to CN 201910076864.4, filed on Jan. 27, 2019, the specifications of which are hereby incorporated in their entireties by reference.

TECHNICAL FIELD OF THE INVENTION

The present invention relates to an occludable venous catheter device, belonging to the technical field of medical device.

BACKGROUND OF THE INVENTION

Venipuncture and the associated intravenous infusion are general techniques most commonly used in clinical departments. In case of long infusion period, flexible venous catheter is most often used for indwelling in the venous lumen. During the indwelling period, flexible venous catheter eliminates the risk of puncture through the vein by the rigid front end of the needle tube; however, in case of no medical liquid infusion in such period, blood coagulation may easily occur in the venous catheter and at the opening due to slow local blood flow or blood stagnation. In spite of measures including anticoagulants such as heparin for sealing the catheter and normal saline for flushing the catheter, thrombosis cannot be prevented in the venous catheter lumen, but may, if falling off, lead to life-threatening acute pulmonary embolism.

When patients move largely, blood is likely to enter the venous catheter lumen, which further accelerates thrombosis.

Even if no thrombus forms in the venous catheter lumen, mural thrombus or fibrin sheath extending along the outer surface of the catheter will be generated due to slow local blood flow or blood stagnation at the catheter opening, not only blocking the venous lumen, but also causing thrombosis on the adjacent venous intima.

Chinese patent 201810470421.9 provides a venous catheter device, which occludes the front-end opening of the venous catheter through an occluding wire isolating from the outer environment, and smoothly put the wire into the venous catheter lumen under guidance. However, the occluding wire moves in a free state between the guide passage opening and the rear-end opening of the venous catheter lumen, and there is no coaxial guide structure, so it is difficult for the occluding wire to enter the venous catheter lumen.

SUMMARY OF THE INVENTION

It is an object of the present invention to provide an occludable venous catheter device.

For achieving the above object, the occludable venous catheter device comprises:

a needle tube for puncturing skin and venous wall, having a bottom portion, a front portion and a front end; a needle tube base connected to the bottom portion of the needle tube; a venous catheter having a venous catheter lumen, a rear-end opening and a front-end opening; a venous catheter base connected to the rear-end opening in a sealed manner, having a chamber; a sealer disposed on the venous catheter base for sealing the chamber of the venous catheter base; an occluding wire covered at least partially by an isolating element which isolates the occluding wire from the outer environment; the needle tube passing through the sealer, the front portion of the needle tube located inside the venous catheter lumen, and the front end of the needle tube passing through the front-end opening and being exposed; wherein, the venous catheter device further comprises a guide passage having a straight tube portion at least at the front of the guide passage and a front-end opening connected to the venous catheter lumen directly or through the chamber; the occluding wire is capable of entering the venous catheter lumen through the guide passage; at least the straight tube portion of the guide passage is coaxial with the venous catheter or the straight tube portion is capable of moving in an externally-isolated manner to a position that a central axis of the straight tube portion coincides with a central axis of the venous catheter; the occluding wire and the guide passage reach directly inside the chamber and are isolated from the outer environment.

The venous catheter can be used not only for injection of fluids such as sterile water, medical liquid and blood, but also for extraction of body fluids such as venous blood, arterial blood, cerebrospinal fluid, pleural effusion for physical examination. The venous catheter is a two-way passage into and out of veins, arteries, pleural cavity, subarachnoid cavity, abdominal cavity and other human body cavities.

The guide passage can be directly a through hole disposed on the sealer, or formed by a hallow passage element passing through the sealer and/or the venous catheter base, a passage element lumen inside the passage element is the guide passage. The guide passage can also be composed of a passage on the sealer in combination with a passage on other component.

The sealer is in a cylinder or bar shape on the whole, matching the shape of venous catheter base, and it is made of deformable elastic materials or hard materials which are not easy to deform; the sealer can also be jointly composed of a flexible elastic part sealed with the venous catheter base and a hard part with the guide passage; the sealer can also be jointly composed of a non-deformable hard part sealed with the venous catheter base and a flexible elastic part with the guide passage; the sealer can be fully made of hard materials and can be rotatably connected with the venous catheter base in a sealed manner, or be a hard sealer with an elastic sealing ring arranged outside the hard sealer to rotatably connected with the venous catheter base in a sealed manner. The section shape of the sealer is preferably circular, or approximately circular or polygon.

In order to make the occluding wire to enter the venous catheter lumen more easy, at least part of the guide passage can be extended to the chamber of the venous catheter base, even to the rear-end opening of the venous catheter.

The occluding wire and the guide passage in a static or relative movement state can directly touch the fluid inside the chamber of the venous catheter base, and the fluid inside the chamber of the venous catheter base outflows through the clearance between the guide passage and the occluding wire and touches the occluding wire and the guide passage, which is the fluid communication as mentioned above.

The guide passage can have a plurality of convexes and/or a plurality of concaves at the internal surface of the guide passage to prevent fluid overflow when the occluding wire is in static or axial movement state, forming a transition fit with the outer surface of the occluding wire to allow gas but not fluid to pass through; The internal surface of the guide passage forms an interference fit with the outer surface of the occluding wire to allow neither fluid nor gas to pass through.

The isolating element can be a deformable capsule structure extended from the sealer; or a hollow thin-walled and externally-sealed flexible isolating element which is easy to deform under force and can be in tube, sleeve, disc, blade, butterfly wing or paddle shapes; or a hollow and externally-sealed hard isolating element that is not easy to deform under force and can be in tube, disc, blade, butterfly wing or paddle shapes; or an externally-sealed isolating element in tube, sleeve, disc, blade, butterfly wing or paddle shapes jointly composed of a hollow thin-walled flexible part which is easy to deform under force and a hollow hard part which is not easy to deform under force. A chamber of the isolating element can be communicated with the part of the chamber of the venous catheter base contacting the infusion fluid through the guide passage.

After the needle tube is detached from the venous catheter or completely removed, the constraint of the needle tube on rotation and translation of at least the straight tube portion of the guide passage is released, so that a central axis of at least the straight tube portion of the guide passage can move to the position coinciding with the central axis of the venous catheter. Coincidence refers to that both are collinear and coaxial, and the occluding wire is easier to pass through the guide passage and the chamber of the venous catheter base, and enter the front end of the venous catheter.

When the central axis coincide, the long and thin occluding wire extending from the front-end opening of the guide passage is easier to enter the venous catheter lumen, and ultimately occlude the front-end opening of the venous catheter.

The guide passage can also be wholly in straight tube shape, or can be a straight tube part connecting with other linear parts angularly, or connecting with other curvilinear parts.

Preferably, the venous catheter device further comprises an infusion connecting pipe having an infusion connecting pipe lumen, which can be connected with the venous catheter base so that the infusion connecting pipe lumen is connected to the chamber of venous catheter base.

One solution is that the infusion connecting pipe is connected to the chamber of venous catheter base through the sealer. In such way, no branch is disposed at the side of the venous catheter base, which facilitates better contact between the tape and skin in use, reduces or eliminates dead cavities in the chamber of venous catheter base, and reduces eddy when flushing the chamber of venous catheter base with normal saline.

Preferably, in order to make the front-end opening of the guide passage closer to the rear-end opening of the venous catheter and guide effect more reliable, the straight tube-shaped guide passage or the straight tube portion of the guide passage is capable of moving axially towards the venous catheter in an externally-isolated manner.

Preferably, a solution of combining the needle tube and the occluding wire passage is as follows: at least the straight tube portion of the guide passage is coaxial with the venous catheter; the needle tube passes through the straight tube portion of the guide passage, and the needle tube front portion is located inside the venous catheter lumen; when the needle tube is removed, the occluding wire is capable of entering into the venous catheter lumen through the straight tube portion of the guide passage; the coaxial structure is pre-set, which saves the step of moving to be coaxial.

Preferably, another solution is that an unclosed needle tube passage is provided, the needle tube passage passes through the sealer, and the needle tube front end is capable of being exposed from the front-end opening of the venous catheter through a front-end opening of the needle tube passage; when the needle tube is removed, the medical liquid is capable of being injected into the chamber of venous catheter base through a bottom-end opening of the needle tube passage.

Preferably, in order to make the straight tube-shaped guide passage or the straight tube portion of the guide passage coaxial with the venous catheter through translation, the sealer has a cave for permitting the movement of the guide passage in an externally-isolated manner.

The cave is isolated from the chamber of the venous catheter base by a deformable membrane. The membrane can be a part of the sealer or a connecting part of the venous catheter base. The guide passage part of different axis can be moved to the coaxial position after the needle tube is removed. The cave provides a space for the movement.

Preferably, another idea of achieving coaxial position by movement is that the sealer or a portion of the sealer having the guide passage is rotatably connected inside the venous catheter base, and a rotation axis of the sealer is parallel to the central axis of the venous catheter; the vertical distance between the central axis of the guide passage and the rotation axis is equal to the vertical distance between the central axis of the venous catheter and the rotation axis.

Preferably, for better rotation, a rotation handle is disposed on the sealer, and the venous catheter base has a limiting structure and/or a guiding structure for allowing the rotation handle to rotate around the venous catheter base.

Preferably, to avoid the bending of the occluding wire during its travel, a length of the straight tube portion of the guide passage is greater than or equal to a distance from the front-end opening of the guide passage to the venous catheter rear-end opening.

Preferably, to ensure that there is no difficulty for the occluding wire to travel in the venous catheter lumen due to its own bending, the length of the straight tube portion of the guide passage is greater than or equal to ½ of the length of the venous catheter.

Preferably, a further reliable design is that the length of the straight tube portion of the guide passage is greater than or equal to the length of the venous catheter.

Preferably, the length of the straight tube portion of the guide passage is greater than or equal to the distance from the front-end opening of the guide passage to the front-end opening of the venous catheter.

Preferably, at least one circumferential area between the guide passage and the outer surface of the occluding wire is for isolated contact of fluid to prevent the medical liquid from entering the chamber of the isolating element.

Preferably, to accommodate the air in the isolating element when it is deformed, especially for the corrugated tubular isolating element, a fluid transfer element having a lumen is connected with the isolating element which has a chamber, and the chamber of the isolating element is in communication with the lumen of the fluid transfer element.

Preferably, to easily drive the occluding wire and isolating element to move, the occluding wire has a tail section which is connected with a control handle; a bottom end of the isolating element of the occluding wire is connected to portion of the control handle in a sealed manner; the fluid transfer element is disposed in a control handle lumen, and the chamber of the isolating element of the occluding wire is communicated with the fluid in the lumen of the fluid transfer element.

Preferably, in order to reduce the pressure on the venous catheter wall caused by the increase of the deflection of the venous catheter during the occlusion, the occluding wire having a front section is hollow at least in the front section, forming an occluding wire lumen, with a blind end at the top of the occluding wire; the occluding wire with the hallow front section does not significantly improve the deflection of the venous catheter.

Preferably, a solution of occlusion and medical liquid infusion passage is that the occluding wire is hallow in whole, forming the occluding wire lumen, with an opening at an end of the occluding wire and the blind end at the top of the occluding wire, and at least one side hole in the front section; when the front section of the occluding wire retreats to the chamber of venous catheter base, the medical liquid can enter the occluding wire lumen through the opening at the end and outflow through the side hole, and then it is injected into the vein through the venous catheter.

Preferably, due to the relatively small outer diameter but large travel distance of the occluding wire, the occluding wire having a tail section is hallow at least in the tail section, forming an occluding wire lumen, in which a pushing guide wire made of metal, carbon fiber and other materials with higher deflection but smaller outer diameter can be inserted.

Preferably, a pushing guide wire is capable of entering the occluding wire lumen to drive the occluding wire moving forward, and can also help with retreating if the relevant connection is configured.

Preferably, due to the high deflection of the pushing guide wire, when the venous catheter is in occluded state, the length of the pushing guide wire do not enter the venous catheter lumen or enters the lumen less than ½ of the length of the venous catheter.

The pushing guide wire guides the occluding wire top to move towards the front-end opening of the venous catheter, and then it can be retreated to the original position or the rear-end opening of the venous catheter, or retreated to the original position along with the occluding wire after completion of occlusion.

The pushing guide wire can assist the occluding wire top to move towards the rear-end opening of the venous catheter. At this time, the pushing guide wire stays at the rear-end opening of the venous catheter and does not move forward, and then drives the occluding wire to move towards the front-end opening of the venous catheter. In this process, the venous catheter serves as the guide for the occluding wire to move forward.

The assistance of the pushing guide wire to the occluding wire comprises push and/or support.

The top of the hollow occluding wire can also be set as a non-blind end, the outer surface of the top portion of the occluding wire can occlude the front-end opening of the venous catheter, and the top portion of the pushing guide wire can occlude the top-end opening of the hollow occluding wire.

The bottom ends of the occluding wire and the pushing guide wire can be respectively connected to the control handle which is convenient for external force application, and the bottom end of the isolating element of the occluding wire is connected with the occluding wire in a sealed and fixed manner directly or through the control handle of the occluding wire.

Preferably, in order to further ensure that the venous catheter device is isolated from the outer environment in use, the pushing guide wire is also disposed in an isolating element, and it can be directly and fixedly connected with the bottom end of the isolating element, or can be connected with the bottom end of the isolating element through the control handle of the pushing guide wire in a sealed and fixed manner.

Preferably, in order to better control the occluding wire, the pushing guide wire and the isolating element outside the venous catheter base, the device further comprises a housing assembly connected with the guide passage; the housing assembly can be bar-shaped, disc-shaped, etc., and relevant grooves and other accommodation and guiding structures are disposed therein; the occluding wire and the isolating element are at least partially located inside the housing assembly.

Preferably, in order to make the front end of the sharp needle tube entering the venous lumen be covered by the front end of the venous catheter when it continues to move during venipuncture and achieve safe needle travel, the needle tube base is connected with an elastic element which is capable of driving the venous catheter base to move axially.

Preferably, for use of the elastic element, the needle tube base is connected to a blade-shaped handle with a bending front end. When a finger is placed against the bending front end, it can eliminate the backward movement of the needle tube caused by the elastic element.

Preferably, the needle tube base is connected with two blade-shaped handles respectively with a bending front end, defined as a right handle and a left handle, extending to an upper surface of the venous catheter base; the venous catheter base has a protruding or concave mating structure between the two blade-shaped handles.

Preferably, to avoid blood coagulation at low temperature, the occluding wire and/or the guide passage is connected with a heat generating element.

The heat generating element can be a metal heating wire or an element which generates heat by non-direct contact electromagnetic induction; the heat generating element can be embedded in the hollow occluding wire, and the bottom end of the occluding wire is connected with a power supply and an electronic control module. In the occluding state, the temperature of the venous catheter in the venous lumen, especially the top part, is equal to or higher than the temperature of the blood in the vein, so as to effectively avoid blood coagulation on the venous catheter.

In the present invention, the control handles, such as rotation handles, which are affected by external force, can be driven manually or by a driving device such as a motor.

The beneficial effect of the invention is as follows:

1. The occluding wire can smoothly enter the venous catheter lumen under continuous guidance or intermittent but coaxial guidance.
2. During the indwelling period with no medical liquid infusion, the occluding wire fully occludes the top opening of the venous catheter, so that blood cannot enter the venous catheter lumen, eliminating the risk of thrombosis in the venous catheter lumen.
3. The cone-shaped head of the occluding wire can partially extend the top opening of the venous catheter in the occluded state, so as to eliminate local dead blood cavities and minimize the formation of mural thrombus, fibrin sheath, venous thrombus.
4. Active and sensitive blood return and safe needle insertion is realized in the process of venipuncture.
5. At least the heat generating element disposed at the top of occluding wire can significantly increase the temperature at the top opening of venous catheter, so as to minimize the risk of blood coagulation.

6. In the connected state, the medical liquid can pass by the heat generating element at the top of occluding wire, which not only facilitates the heat balance of human body but also minimizes the risk of blood coagulation due to low temperature.
7. In the connected or occluded state, at least the heat generating element at the top of occluding wire can avoid the risk of infection caused by reduced leukocyte activity due to local low temperature.

BRIEF DESCRIPTION OF THE DRAWINGS

The drawings, not limiting the present invention, are as follows.

DETAILED DESCRIPTION OF THE INVENTION

Figure 1A:
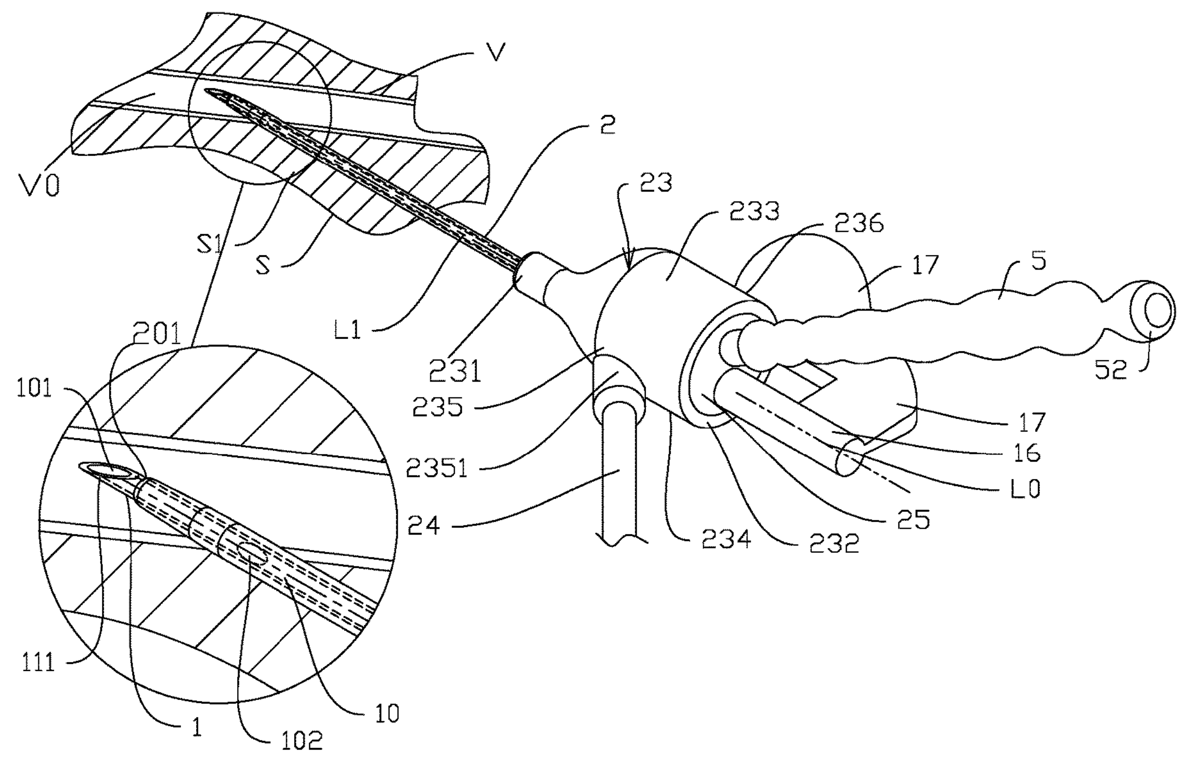
FIGS. 1A, 1B, 1C, 1D, 1E and 1F are perspective/sectional views of an occludable venous catheter device according to Embodiment 1.

The reference numbers in the drawings of the present invention will not necessarily be interpreted in detail in the embodiments if they have been described in previous embodiments. The embodiments, not limiting the present invention, are described as follows.

Embodiment 1

As shown in FIGS. 1A, 1B, 1C, 1D, 1E and 1F, the occludable venous catheter device of Embodiment 1 of the present invention comprises: a rigid needle tube 1 for puncturing skin S and venous wall V, a needle tube base 16, a venous catheter 2, a venous catheter base 23, a sealer 25, an occluding wire 3, a occluding wire guide passage 40 and an isolating element 5; the needle tube 1 is hollow inside and has a needle tube lumen 10, a bottom portion 15, a front portion 11 and a sharp front end 111, the front portion 11 of the needle tube 1 is located inside the venous catheter lumen 20, the sharp front end 111 is exposed from a front-end opening 201 of the venous catheter 2 during puncture, the needle tube lumen 10 has an opening 101 at the front end 111 of the needle tube 1, and the front portion 11 of the needle tube 1 has a side opening 102 near the front end 111 of the needle tube 1; a connecting portion 12 of the needle tube 1 is located in the area of a front end 231 of the venous catheter base 23, a middle portion 13 of the needle tube 1 is located in a chamber 230 of the venous catheter base 23, a passing portion 14 of the needle tube 1 is located in the sealer 25, a bottom portion 15 of the needle tube 1 is fixed in the needle tube base 16, and the needle tube base 16 is connected with a needle tube base handle 17; the relatively flexible hollow venous catheter 2 can be made of PU, FEP and other materials, and comprises a front portion 21 and a rear portion 22. The front portion 21 of the venous catheter 2 has a tapered front end 211. The medical liquid flows into the vein V through the front-end opening 201 of the venous catheter 2 via the venous catheter lumen 20, and the venous catheter lumen 20 is connected with the chamber 230 of the venous catheter base 23 through a rear-end opening 202; between a front end 231 and a rear end 232 of the venous catheter base 23 is an upper surface 233, a lower surface 234, a left side surface 235 and a right side surface 236. The chamber 230 has a smaller front-end opening 2301 in the front end 231 and a larger rear-end opening 2302 in the rear end 232. The front-end opening 2301 is sleeved with the hollow rear portion 22 of the venous catheter 2, and the rear-end opening 2302 of the venous catheter base 23 is filled with the sealer 25; the left side surface 235 of the venous catheter base 23 has a hollow infusion collateral 2351 which is connected with an infusion connecting pipe 24, and the chamber 230 of the venous catheter base 23 is communicated with an infusion connecting pipe lumen 240; a front surface 251 of the sealer 25 is adjacent to the chamber 230 of the venous catheter base 23, and a rear end surface 252 faces outward. The sealer 25 comprises a hard portion 25*a* and an elastic portion 25*b*. The hard portion 25*a* can be made of resin PC, as, ABS, etc., the elastic portion 25*b* can be made of elastic materials such as silicone rubber, polyurethane, etc., and the elastic portion 25*b* can close and seal the area it passes through after the needle tube 1 is extracted; the hard portion 25*a* of the sealer 25 has the occluding wire guide passage 40, a straight tube portion 41 is at the front of the guide passage 40, the rear portion 42 is obliquely connected with the straight tube portion 41, and the guide passage 40 has a front-end opening 401 and a rear-end opening 402; the occluding wire 3 can enter the guide passage 40 from the rear-end opening 402 of the guide passage 40; outside the occluding wire 3 is a deformable isolating element 5 in a saccular shape with thin wall, which can be made of flexible film materials such as silicone rubber, polyurethane, polyethylene, EVA, PET, etc. A front end 51 of the isolating element 5 has an opening 501, and a rear end 52 is a blind end. The front end 51 of the isolating element 5 is sleeved in a sealed manner with a cylindrical or flat external convex portion 254 of the hard portion 25*a* of the sealer 25, which can be connected by bonding, hot melting, ultrasonic welding and other methods in a sealed manner. Part of the rear portion 42 of the guide passage 40 is located in the convex portion 254, and the rear-end opening 402 of the guide passage 40 is located on a rear surface 2541 of the convex portion 254; the parts of the occluding wire 3 that may be in direct contact with the chamber 230 of the venous catheter base 23 and/or in communicated with fluid are all located in a chamber 50 of the isolating element 5. In this embodiment, an end 341 of the occluding wire 3 is completely located in the chamber 50 of the isolating element 5.

As shown in FIG. 1A, the needle tube 1 and the venous catheter 2 puncture the skin surface S, a subcutaneous tissue Si and the venous wall V, the sharp front end 111 of the needle tube 1 enters a venous lumen V0, and venous blood flows into needle tube lumen 10 and is observed by the operator through transparent venous catheter 2 at the side opening 102 at the front end 111 of the needle tube 1, so as to confirm the success of puncture.

Figure 1B:
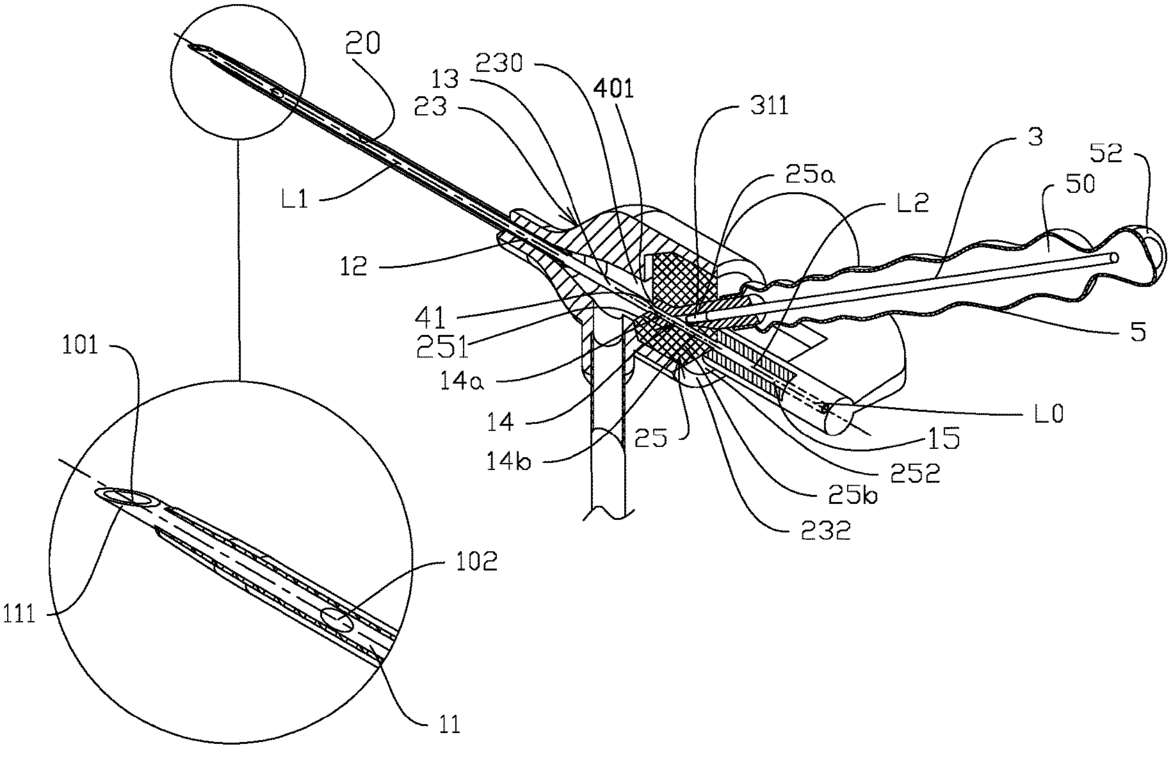

In the initial state as shown in FIG. 1B, a central axis L0 of the needle tube 1, a central axis L2 of the straight tube portion 41 of the guide passage 40, and a central axis L1 of the venous catheter are collinear. A portion 14*a* of the passing portion 14 of the needle tube 1 is located in the straight tube portion 41 of the guide passage 40 of the hard portion 25*a* of the sealer 25, and another portion 14*b* of the passing portion 14 of the needle tube 1 passes through the elastic portion 25*b* of the sealer 25; at this time, the front-end opening 401 of the guide passage 40 is occupied by the needle passing portion 14*a*, and the occluding wire 3 cannot enter the chamber 230 of the venous catheter base 23.

Figure 1C:
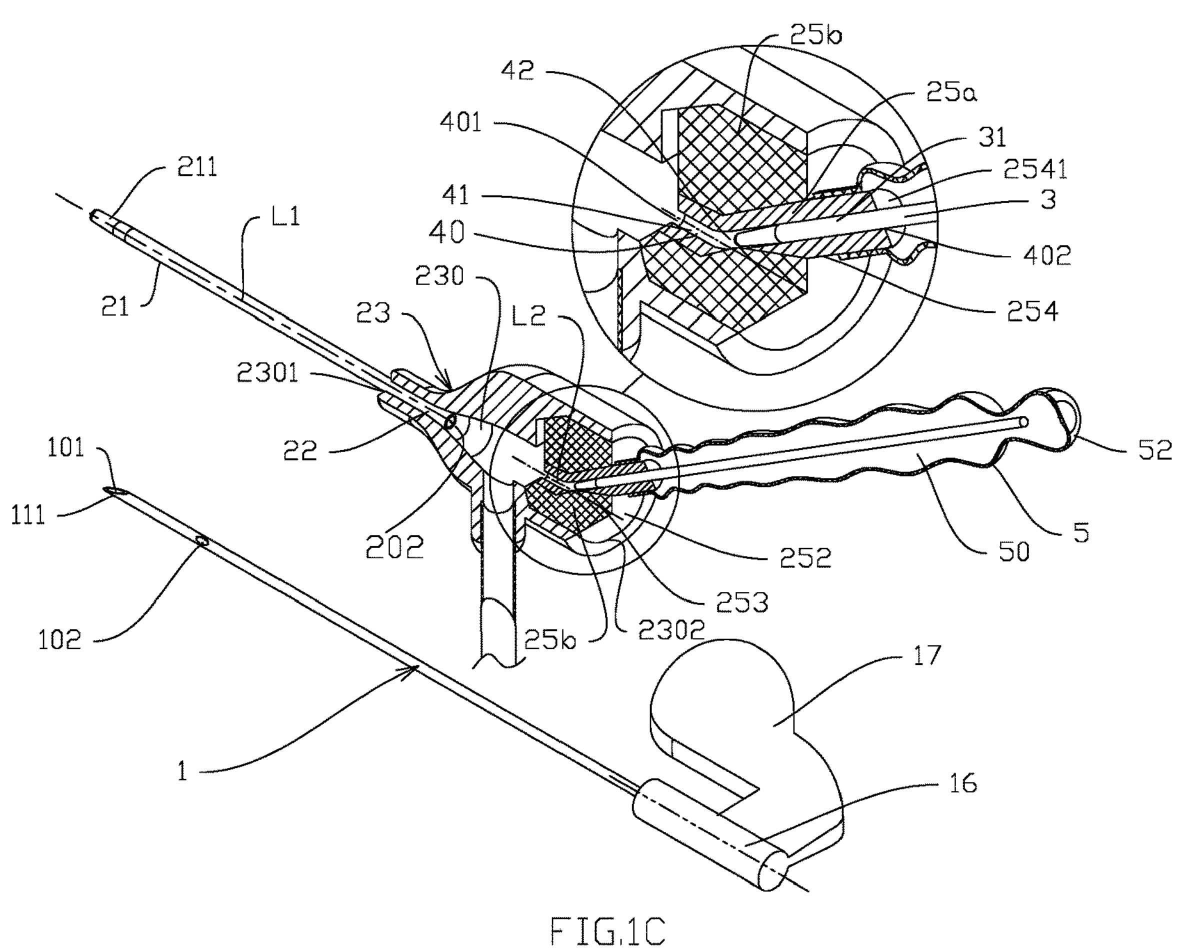
Figure 1D:
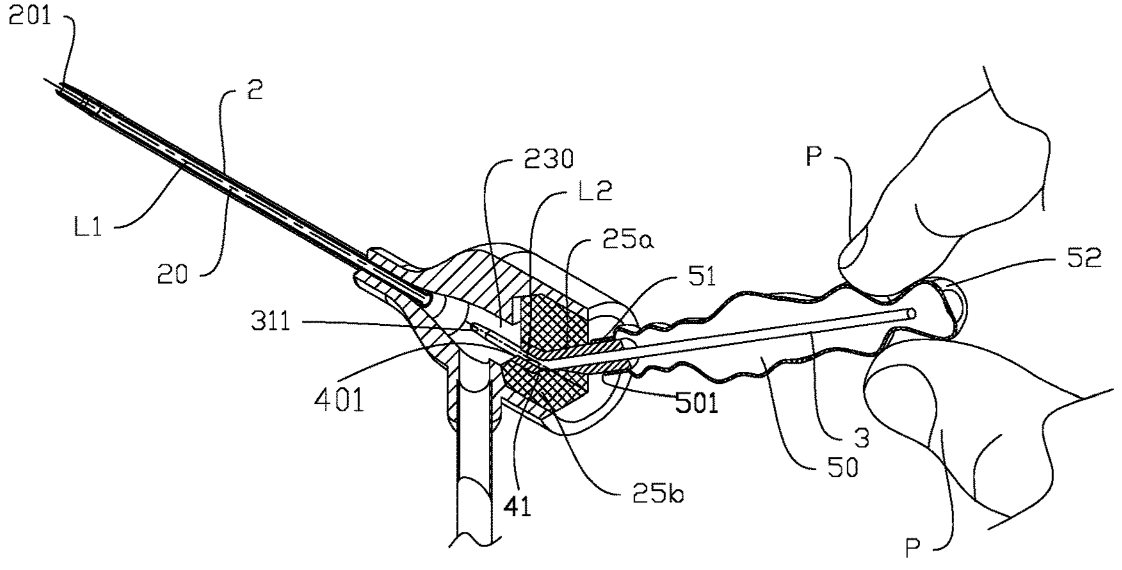
Figure 1E:
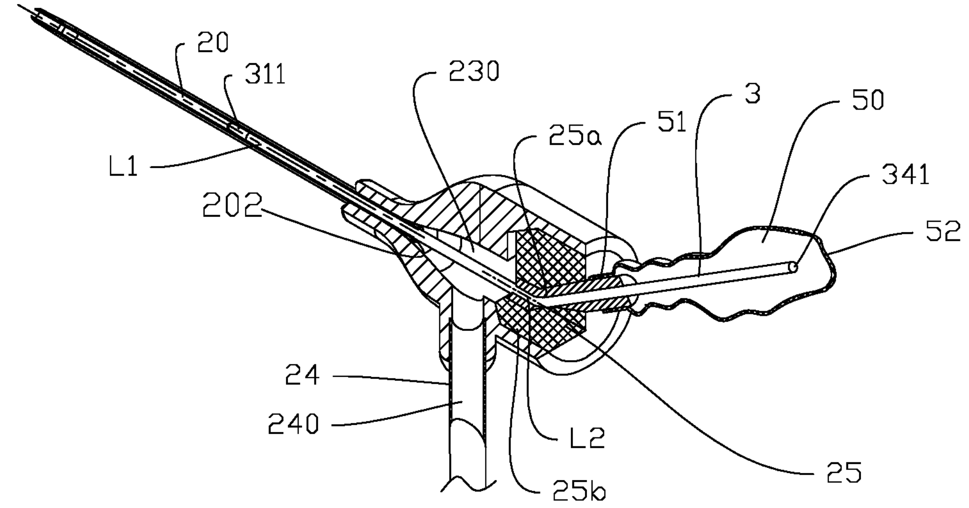

As shown in FIG. 1C, after venipuncture is completed, the needle tube 1 is removed, and the elastic portion 25*b* of the sealer 25 closes a linear area 253 through which the needle tube 1 passes and isolates it from the outside due to the rebound deformation of the material. At this time, the front-end opening 401 of the guide passage 40 is connected with the chamber 230 of the venous catheter base 23; as shown in FIG. 1D, because the straight tube portion 41 of the guide passage 40 is coaxial with the venous catheter 2, that is, the central axis L2 of the straight tube portion 41 of the guide passage 40 is collinear with the central axis L1 of the venous catheter 2, the occluding wire 3 enters into the chamber 230 of the venous catheter base 23 under the coaxial guidance of the straight tube portion 41 of the guide passage 40; as shown in FIG. 1E, the occluding wire 3 enters the venous catheter lumen 20 through the rear-end opening 202 of the venous catheter 2; as shown in FIG. 1F, the occluding wire 3 finally blocks the front-end opening 201 of the venous catheter 2, and the isolating element 5 deforms, and compresses and accumulates towards the direction of rear surface 252 of the sealer 25; this coaxial straight entry design makes it easier for the occluding wire 3 to enter the venous catheter lumen 20, with far better effect than the method of oblique entry with different axes.

Figure 1F:
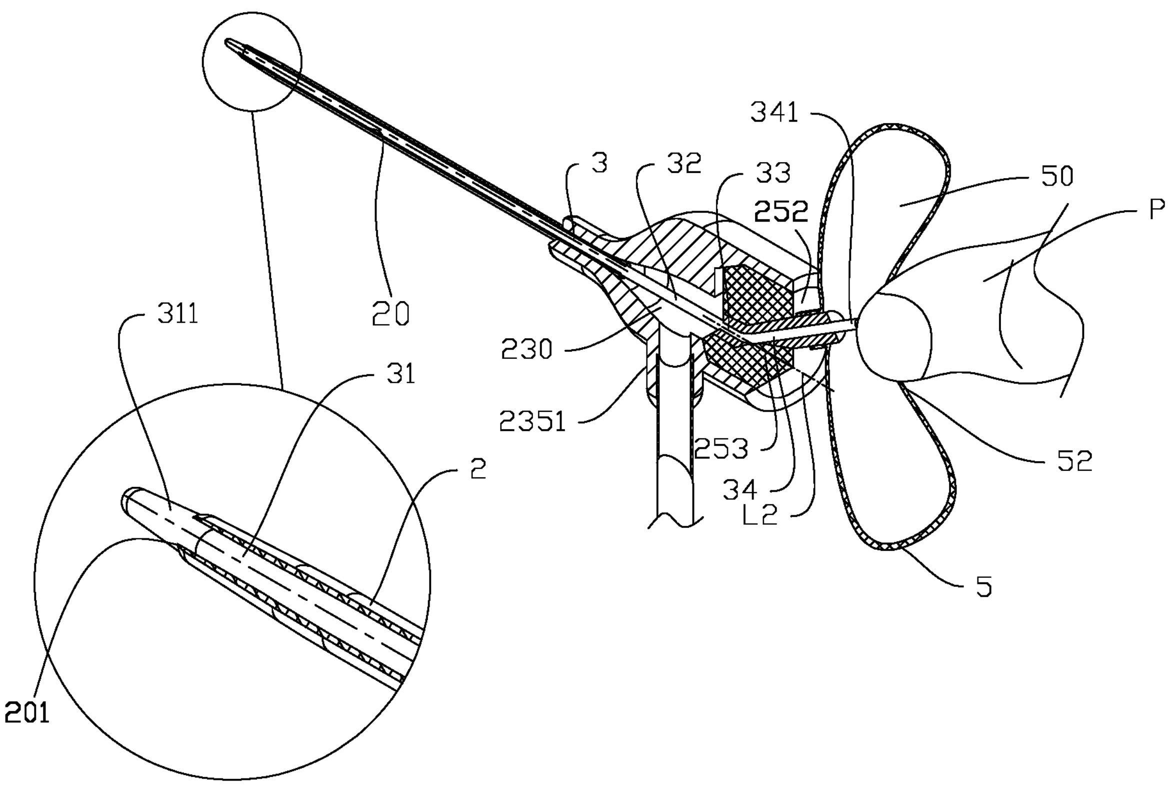

As shown in FIG. 1F, in the occluded state, the part of the occluding wire 3 located in the venous catheter lumen 20 is defined as a front section 31 having a blind end 311, the part located in the chamber 230 of the venous catheter base 23 is defined as a middle section 32, the part located in the straight tube portion 41 of the guide passage 40 is defined as a rear section 33, and the rest is defined as a tail section 34. The end 341 of the tail section 34 is located in the chamber 50 of the isolating element 5, the blind end 311 of the front section 31 of the occluding wire 3 is tapered and extends from the front-end opening 201 of the venous catheter 2, which minimize the risk of blood vortex during occlusion; the blind end 311 of the occluding wire 3 and the front-end opening 201 of the venous catheter 2 contact with each other as blood barrier, that is, blood cannot pass through the clearance between the venous catheter 2 and the occluding wire 3, which can be interference fit with each other or conformal fit with each other.

In this embodiment, the occluding wire 3 is a solid wire, which can be made of resin materials such as PU, PA, PET and PDFE by extrusion or molding, or metal materials such as nickel-titanium alloy; when in use, the operator's finger P presses and pinches the flexible membrane-shaped isolating element 5 to fix the occluding wire 3 in its chamber 50, and drives the occluding wire 3 forward or backward. Specifically, the operator can press and pinch the bottom end 52 of the isolating element 5 and the end 341 of the occluding wire tail section 34 in the isolating element 5.

Embodiment 2

Figures 2A, 2B:
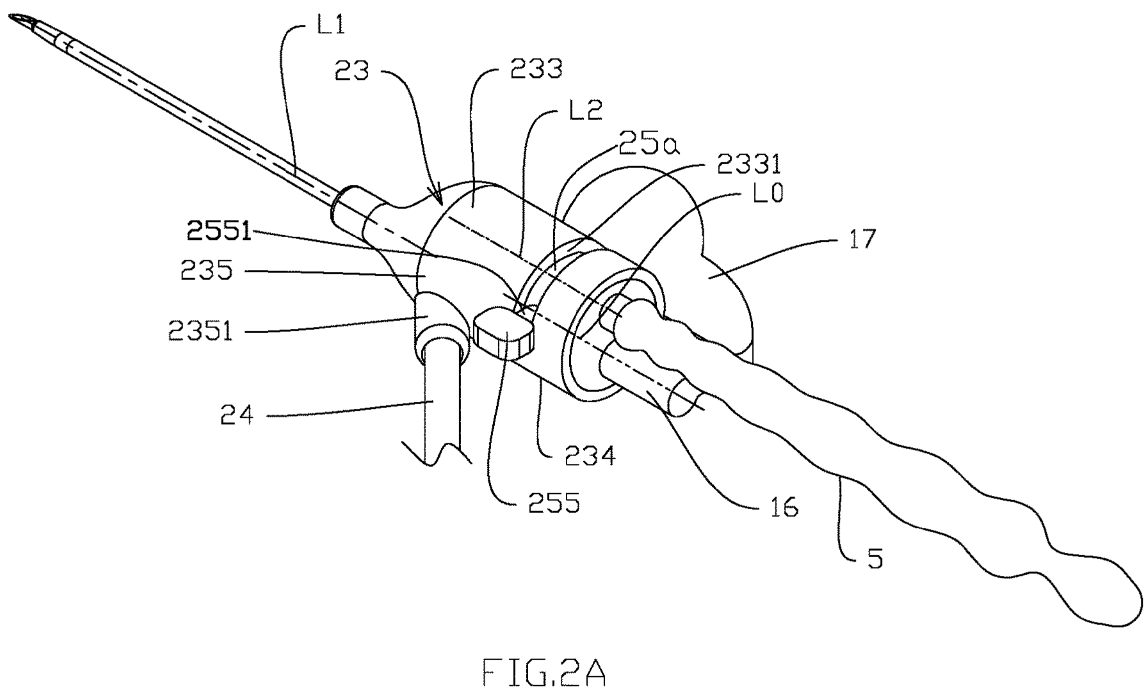
FIGS. 2A, 2B, 2C, 2D, 2E, 2F, 2G, 2H and 2I are perspective/sectional views of the occludable venous catheter device according to Embodiment 2.
Figures 2C, 2D:
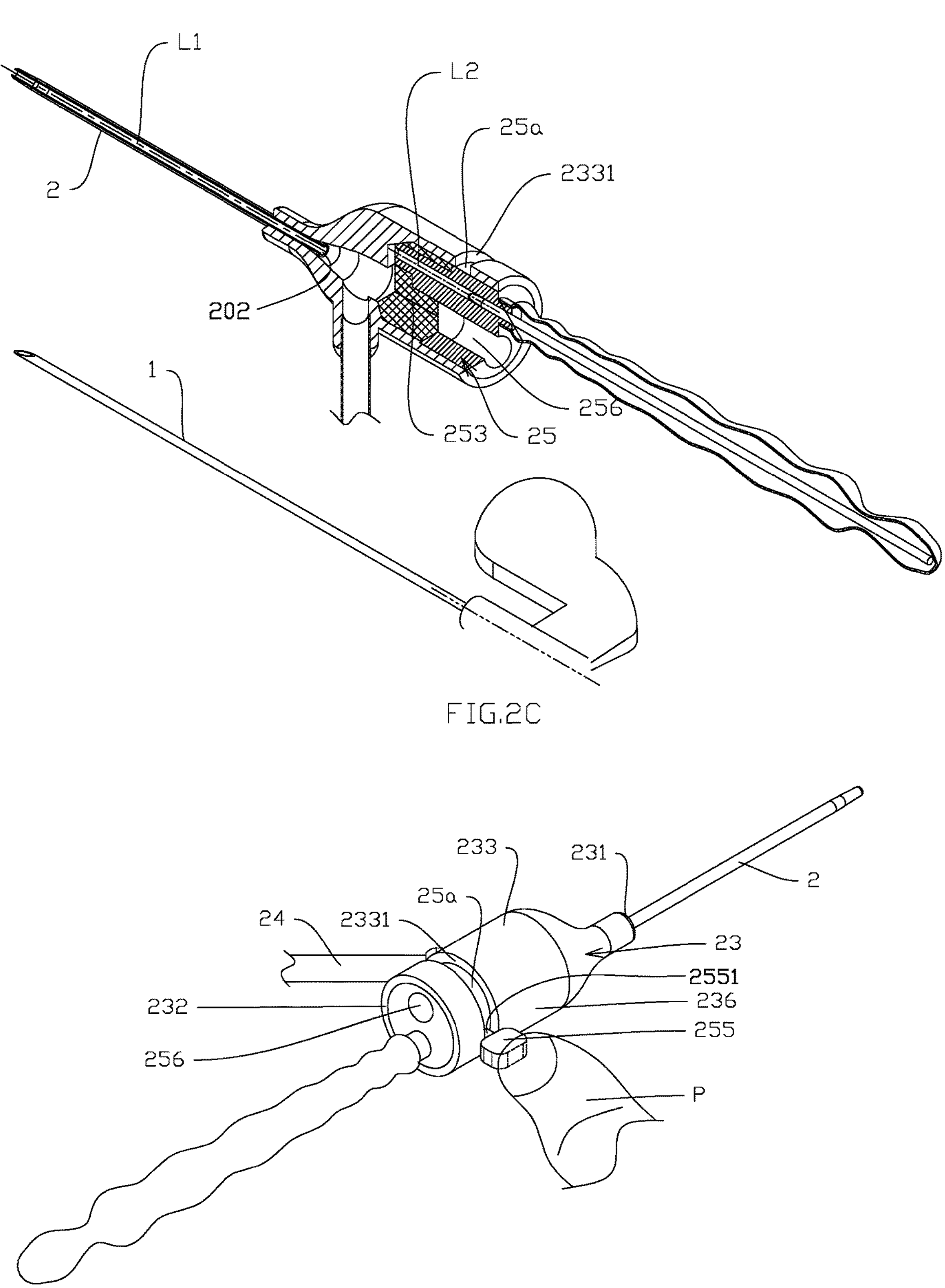
Figures 2E, 2F:
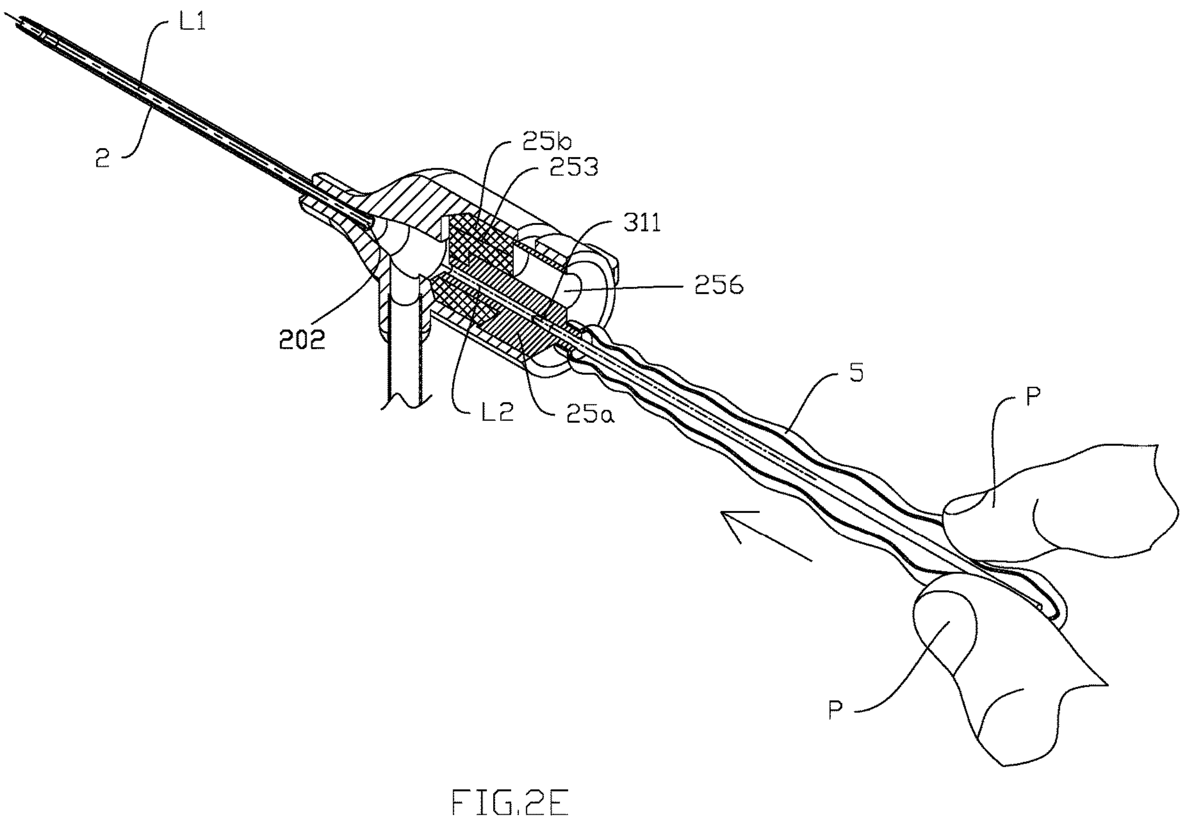
Figure 2G:
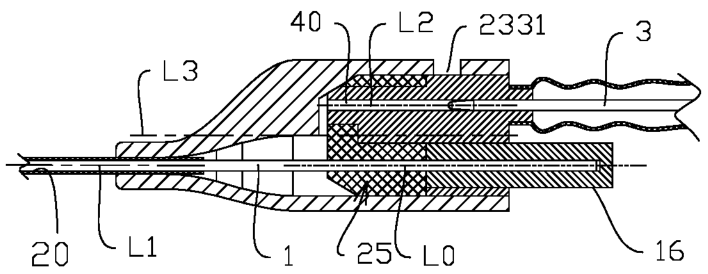
Figure 2H:
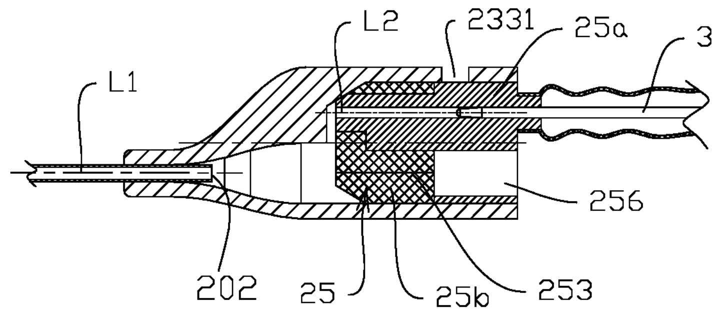
Figure 2I:
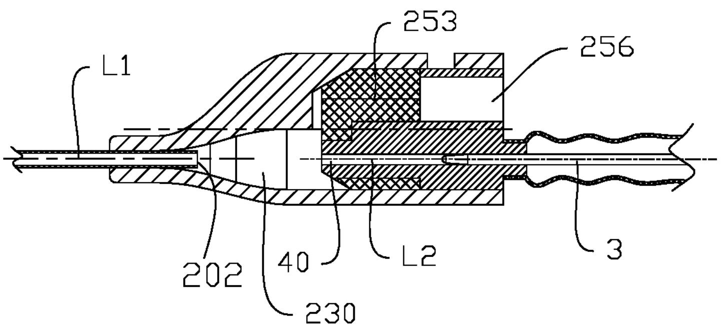

FIGS. 2A, 2B, 2C, 2D, 2E, 2F, 2G, 2H and 2I show a venous catheter device of Embodiment 2, the biggest difference from Embodiment 1 is that, in the initial state, the central axis L2 of the straight tube portion 41 of the guide passage 40 is not coaxial but parallel to the central axis L1 of the venous catheter 2. FIG. 2A shows that the needle tube base 16 is located below the isolating element 5, and the upper surface 233 of the venous catheter base 23 has an arched window 2331, a part of the hard portion 25*a* of the sealer 25 is exposed in the arched window 2331. The hard portion 25*a* of the sealer 25 is connected with a rotation handle 255, which is connected with the hard portion 25*a* of the sealer 25 through a neck 2551; the section view of FIG. 2B shows that the blind end 311 of the front section of the occluding wire 3 is located in the guide passage 40 and adjacent to the rear-end opening 402. The front-end opening 401 of the guide passage 40 faces a convex 2303 of the chamber 230 of the venous catheter base 23, and the occluding wire 3 cannot enter the venous catheter lumen 20; the hard portion 25*a* and the elastic portion 25*b* of the sealer 25 are interlaced with each other by means of secondary molding, bonding and interference fit, and they can move synchronously; when there is no interference of the needle tube 1 in the venous catheter lumen 20, the rotation handle 255 rotates from the left side of the arched window 2331 to the right side, which can make the sealer 25 rotate and move with the centerline L3 of the venous catheter base 23 as the axis; FIG. 2C shows that the needle tube 1 is pulled away from the sealer 25, the linear area 253 is closed and isolated from the outer environment, a concave 256 of the needle tube base 16 on the sealer 25 is empty, and the linear area 253 is still located on the extended line of the central axis L1 of the venous catheter 2; as shown in FIG. 2D, the operator's finger P acts on the handle 255 on the hard portion 25*a* of the sealer 25, and drives the handle 255 to rotate from the left side of the arched window 2331 to the right side. When the neck 2551 cannot move, it means that the handle 255 has rotated in place. At this time, the central axis L2 of the straight tube-shaped guide passage 40 is collinear with the central axis L1 of the venous catheter 2. As shown in FIG. 2E, the finger P applies force on the isolating element 5 to drive the blind end 311 of the front section of the occluding wire to move along the direction of the arrow on the central axis L1 of the venous catheter 2; FIG. 2F shows that the blind end 311 of the front section 31 of the occluding wire 3 is tapered and extends from the front-end opening 201 of the venous catheter, thus occluding the venous catheter 2, and the whole isolating element 5 is compressed axially and deformed to both sides; in order to clearly show the principle of achieving coaxial relationship by rotating and moving, the sectional view of FIG. 2G shows that in the initial state, the needle tube 1 is located in the venous catheter lumen 20, the central axis L2 of the straight tube-shaped guide passage 40 is not coaxial but parallel to the central axis L1 of the venous catheter 2, and the rotation axis L3 is located between them; the sectional view of FIG. 2H shows that the needle tube 1 is removed from the sealer 25, and there is no interference factor of rotation and movement at this time; the sectional view of FIG. 2I shows the state after rotation in place. The central axis L2 of the straight tube-shaped guide passage 40 and the central axis L1 of the venous catheter 2 are in a collinear position. In this embodiment, the guide passage 40 is straight in the whole process, without bending and tilting parts. The whole rotation is carried out on the premise of isolating from the external environment, and there is no risk of microorganisms or foreign matters entering the chamber 230 of the venous catheter base 23; when intravenous infusion is needed, the occluding wire 3 only needs to be pulled out from the venous catheter lumen 20 so that it does not occlude the rear-end opening 202 of the venous catheter.

Embodiment 3

FIGS. 3A, 3B, 3C and 3D show a venous catheter device of Embodiment 3, the biggest difference, compared to method of making the central axis L2 of the straight tube-shaped guide passage 40 on the sealer 25 colinear with the central axis L1 of the venous catheter 2 by rotation in an externally-isolated manner in embodiment 2 is that, the guide passage 40 is formed by an independent hollow passage element 4, and the collinearity is realized by translation rather than rotation of external in an externally-isolated manner.

Figure 3A:
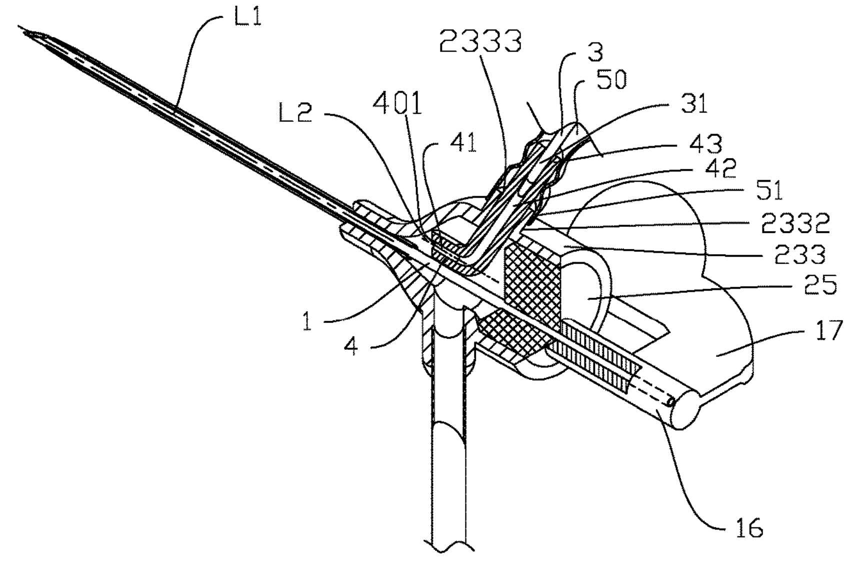
FIGS. 3A, 3B, 3C and 3D are sectional views of the occludable venous catheter device according to Embodiment 3.

As shown in the section view FIG. 3A, there is a tubular convex 2332 on the upper surface 233 of the venous catheter base 23, the tubular convex 2332 is sleeved with the passage element 4, the passage element 4 has an extended section 43 extending from the outer surface 2333 of the tubular convex 2332 of the venous catheter base 23, the inner surface of the front end 51 of the isolating element 5 is connected with the outer surface of the tubular convex 2332 in a sealed manner, and the extended section 43 of the passage element 4 is located in the chamber 50 of the isolating element 5. The passage element 4 can be driven by an external force applied to the extended section 43 to perform translation relative to the tubular convex 2332. The front section of the bending hollow part of the passage element 4 is the straight tube portion 41 of the guide passage 40, the rear section 42 is obliquely connected with the front section 41, and the front section 31 of the occluding wire 3 enters into the rear section 42 of the guide passage 40, the central axis L2 of the straight tube portion 41 of the guide passage 40 is parallel to the central axis L1 of the venous catheter 2, but the sealer 25 can be completely made of elastic material without rotation; in the initial state, the passage element 4 cannot move downward due to the obstruction of the needle tube 1.

Figure 3B:
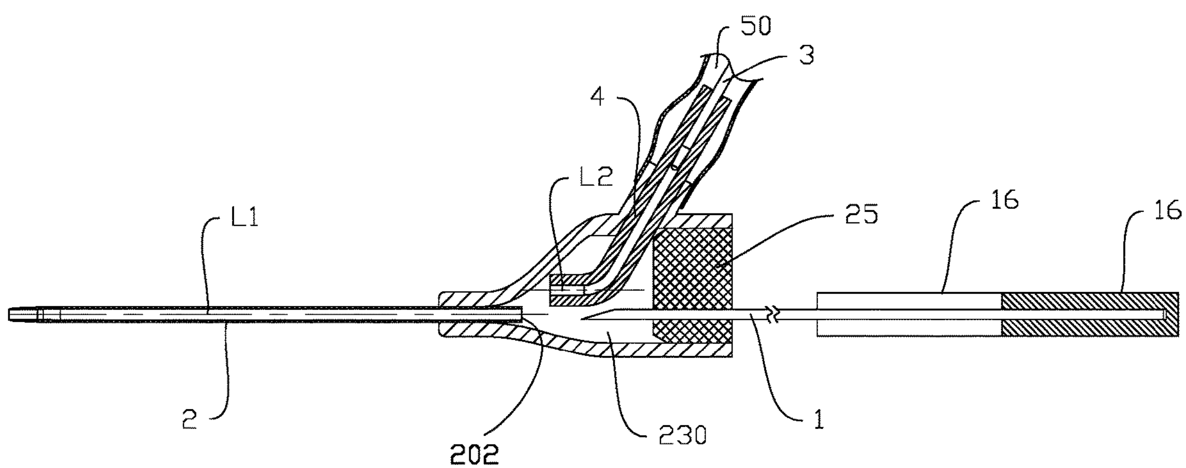

When in use, after successful venipuncture, the needle tube 1 starts to retreat from the sealer 25, and as shown in FIG. 3B, after the needle tube 1 is pulled out, it will no longer hinder the descending of the passage element 4.

Figures 3C, 3D, 4A:
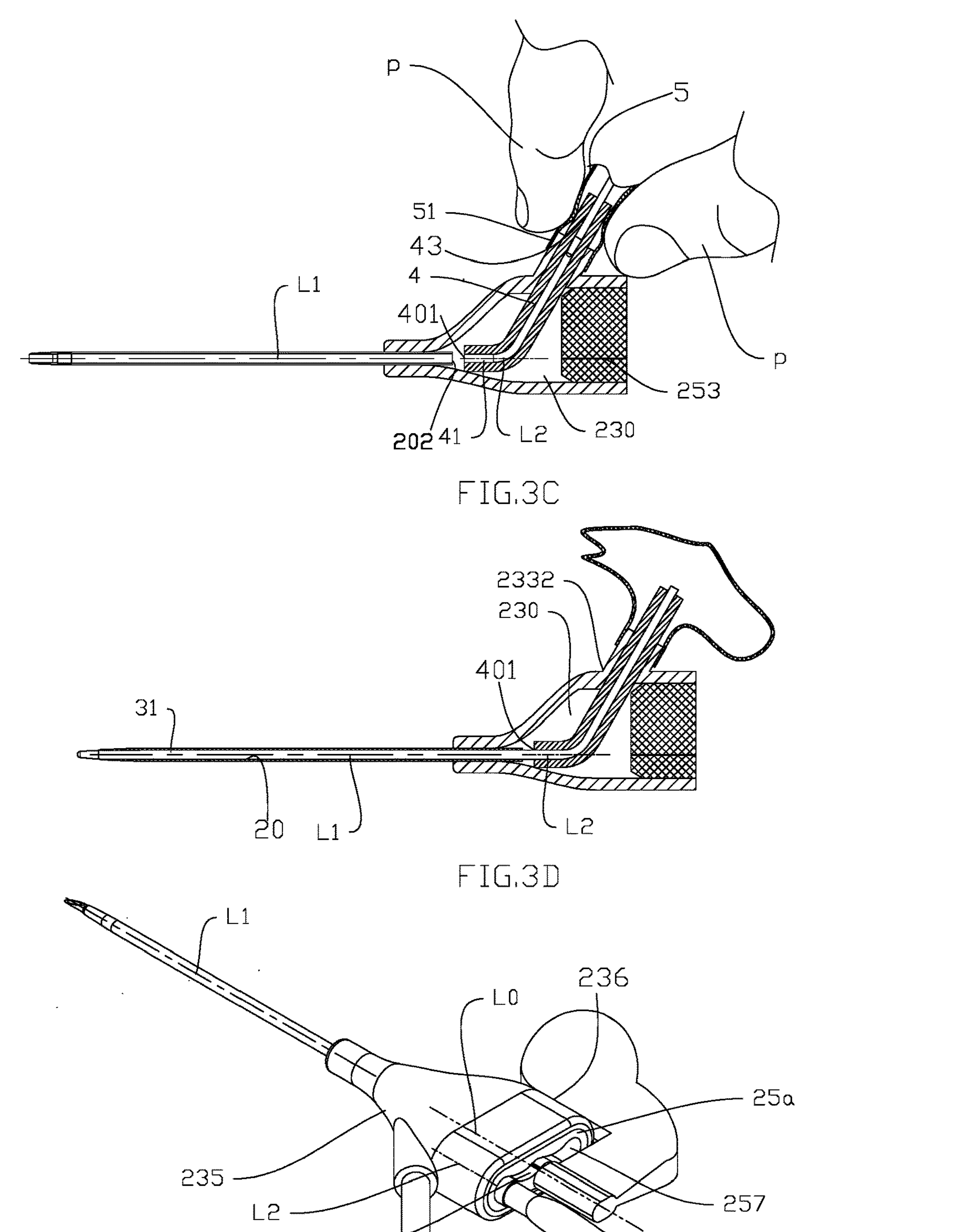
FIGS. 4A, 4B, 4C, 4D and 4E are perspective/sectional views of the occludable venous catheter device according to Embodiment 4.

As shown in FIG. 3C, the finger P pinches the area near the front end 51 of the isolating part to make the flexible isolating element 5 contact the extended section 43 of the passage element 4 and push it downward with force. The passage element 4 descends until the central axis L2 of the straight tube portion 41 is coaxial with the central axis L1 of the venous catheter 2. At this time, the front end of the straight tube portion 41 of the passage element 4 contacts the inner wall of the venous catheter base 23 and cannot continue to move.

As shown in FIG. 3D, the front section 31 of the occluding wire 3 extends from the front-end opening 401 of the guide passage 40 and advances along the central axis L1 of the venous catheter 2 into the venous catheter lumen 20. Due to reliable isolation, microorganisms and other foreign matters in the external environment will not be brought into the chamber 230 of the venous catheter base 23, that is, they will not enter into the venous lumen V0; of course, the tubular convex 2332 on the venous catheter base 23 can also be disposed on the left side surface 235 or the right side surface 236 of the venous catheter base 23.

Embodiment 4

FIGS. 4A, 4B, 4C, 4D and 4E show a venous catheter device of Embodiment 4. Compared with Embodiment 3, in which the central axis L2 of the straight tube portion 41 of the guide passage 40 composed of the independent hollow passage element 4 is moved to the position coaxial with the central axis L1 of the venous catheter 2 by means of translation rather than rotation in an externally-isolated manner, the biggest difference is that, the straight tube-shaped passage element 4, the elastic portion **25*b* of the sealer 25 through which the needle tube 1 passes and the hard portion 25*a* of the sealer 25 are connected with the inner wall of the venous catheter base 23 in a sealed manner; adjacent to the right side surface 236 of the venous catheter base 23, there is a cave 257 between the elastic portion 25*b* and the hard portion 25*a* of the sealer 25, and the right cave 257 is the area through which the needle tube 1 with the shape and volume just can accommodate the elastic portion 25*b*** to pass.

Figure 4B:
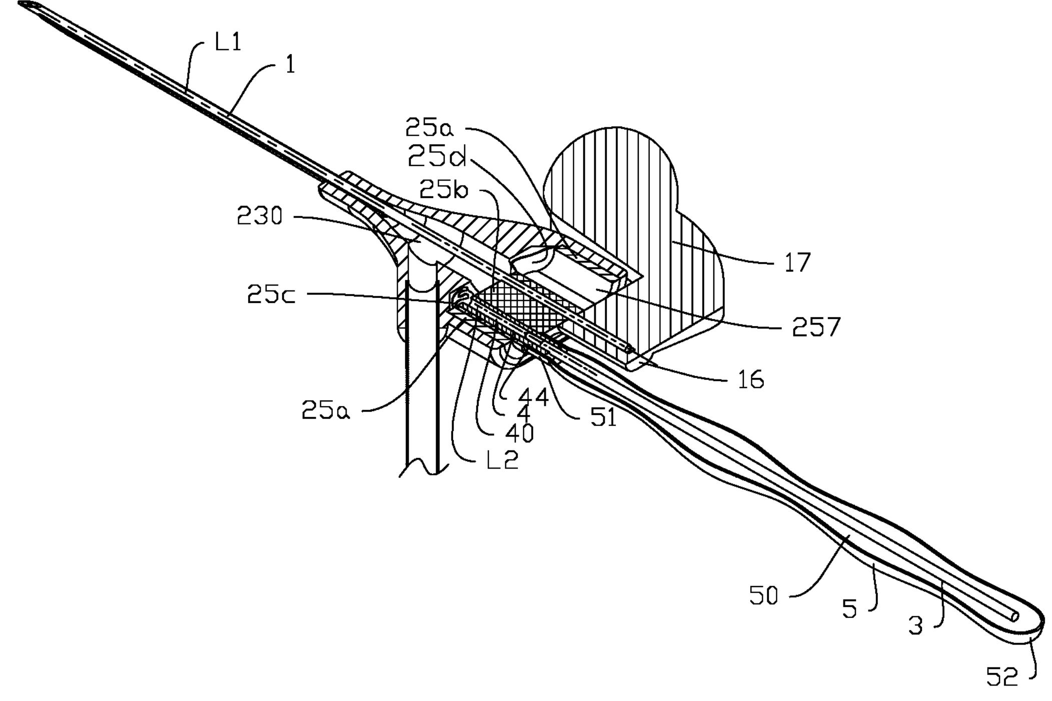

As shown in the section view of FIG. 4B, the elastic portion **25*b* of the sealer 25 can be translated relative to the hard portion 25*a*, and the front edge of the elastic portion 25*b* of the sealer 25 is sealed with the front edge of the hard portion 25*a* through a flexible membrane. The figure shows that the left portion 25*c* of the sealing membrane is bent, and the right portion 25*d* is relatively stretched, the right cave 257 is isolated from the chamber 230 of the venous catheter base 23 by the right portion 25*d* of the sealing membrane; the passage element 4 has an extended section 44 extending from the rear end of the elastic portion 25*b* of the sealer 25, and the outer surface of the extended section 44 is connected with the inner surface of the front end 51 of the isolating element 5 in a sealed manner; when there is no interference of the needle tube 1, the external force acting on the extended section 44 of the passage element 4 can make the elastic portion 25*b* of the sealer 25 perform translation together with the guide passage 40**.

Figure 4C:
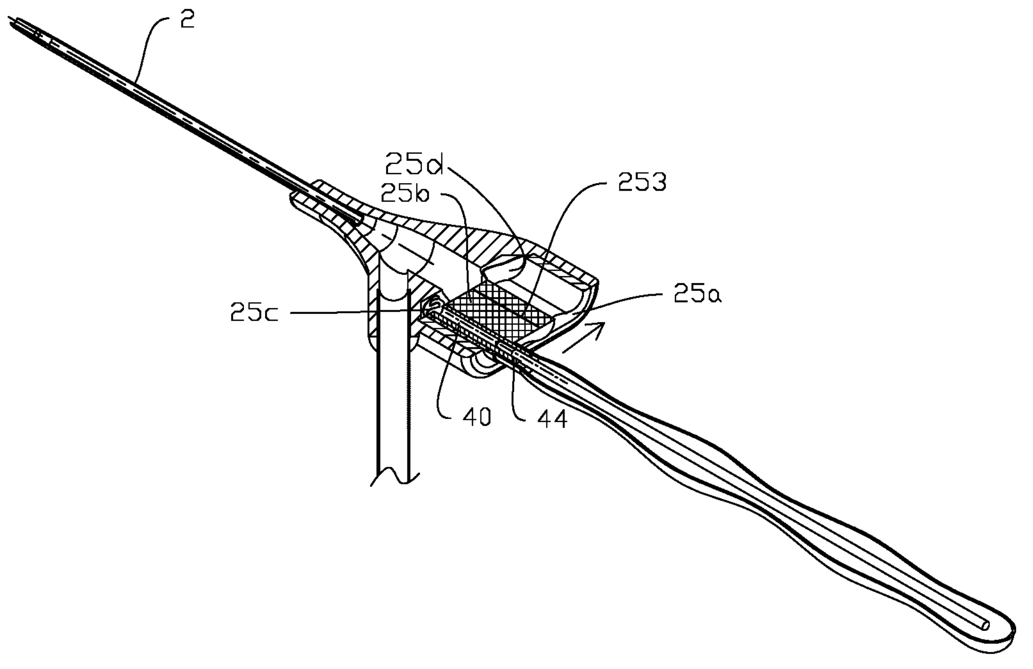

As shown in the section view of FIG. 4C, after successful venipuncture, the needle tube 1 is pulled away from the elastic portion **25*b* of the sealer 25, and the linear area 253 that the needle tube 1 previously passes through is closed and isolated from the outer environment. At this time, the external force acting on the extended section 44 of the passage element 4 can cause the elastic portion 25*b* of the sealer 25 and the guide passage 40** to perform translation in an externally-isolated manner, as shown by the arrow.

Figure 4D:
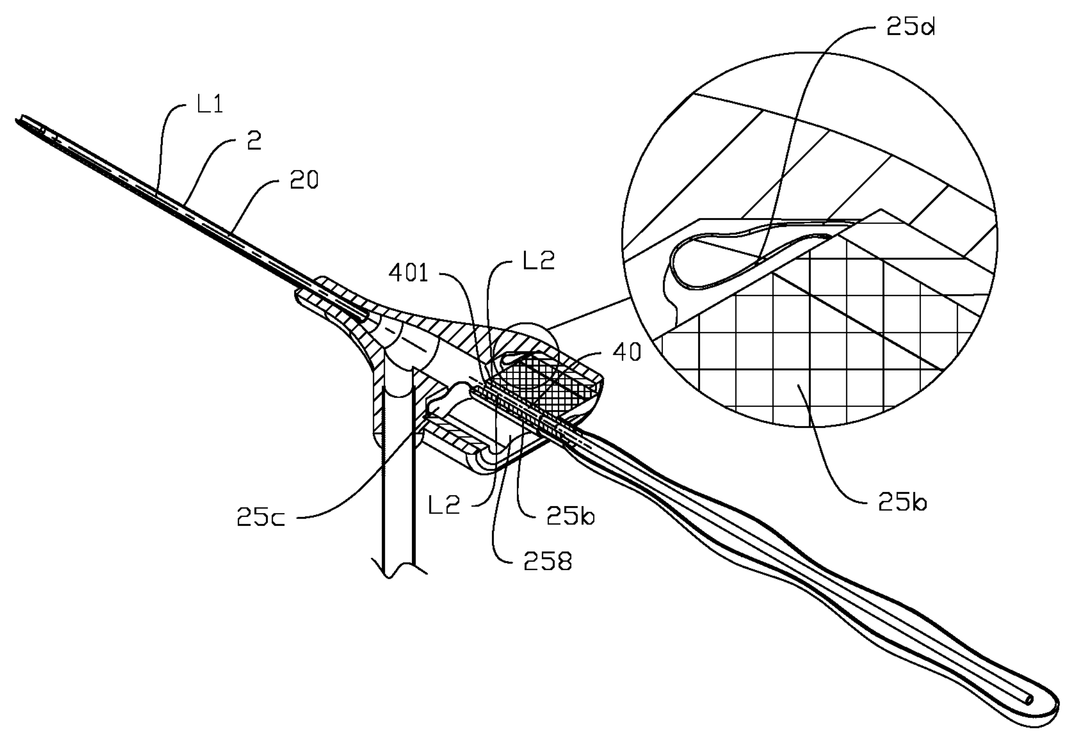

As shown in the section view of FIG. 4D, the elastic portion **25*b* of the sealer 25, together with the guide passage 40, moves to the right cave 257 and fills the cave 257, while the space in front of the elastic portion 25***b* is empty to form a left portion 258; the left portion 25*c* of the sealing membrane is stretched, while the right portion 25*d* is bent; At this time, the central axis L2 of the guide passage 40 is coaxial with the central axis L1 of the venous catheter 2.

Figure 4E:
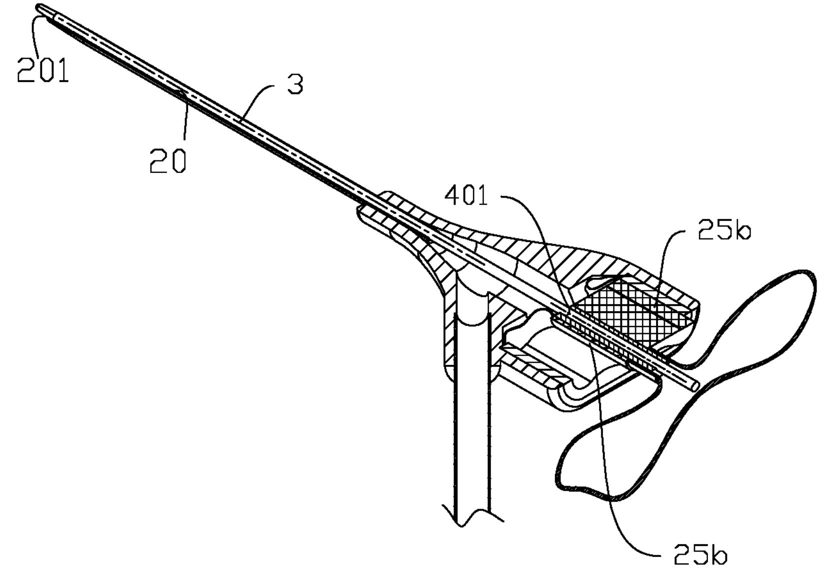

As shown in FIG. 4E, the occluding wire 3 extending from the front-end opening 401 of the guide passage 40 can smoothly enter the venous catheter lumen 20, and finally occlude the front-end opening 201 of the venous catheter 2.

Embodiment 5

FIGS. 5A, 5B, 5C, 5D and 5E show a venous catheter device of Embodiment 5. The solution shown in this embodiment is that after the central axis L2 of the straight tube-shaped guide passage 40 rotates and moves to the position collinear with the central axis L1 of the venous catheter 2, the guide passage 40 moves axially, so that the front-end opening 401 of the guide passage 40 is closer to or directly contacts the rear-end opening 202 of the venous catheter 2, so as to better ensure the entry of the occluding wire 3.

Figure 5A:
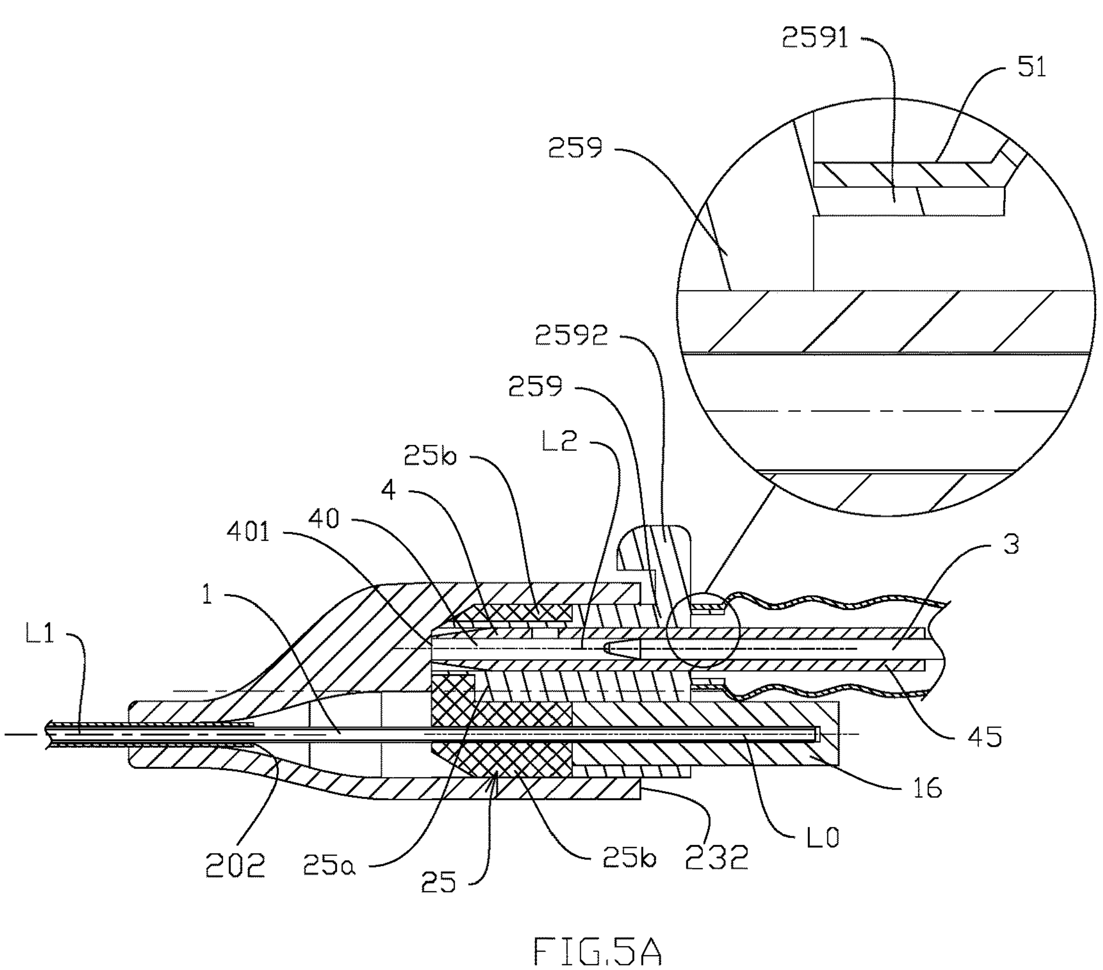
FIGS. 5A, 5B, 5C, 5D and 5E are sectional views of the occludable venous catheter device according to Embodiment 5.

The section view FIG. 5A shows that the needle tube 1 and the passage element 4 penetrate in the sealer 25, the front end part of the needle tube base 16 is embedded in the concave 256 of the sealer 25, the sealer 25 is composed of a hard portion 25*a* and an elastic portion 25*b*, the passage element 4 is a straight tube as a whole, and an extension portion 45 extends from the rear end of the hard portion 25*a* of the sealer 25, the rear end of the hard portion 25*a* of the sealer 25 wrapping the passage element 4 has an extended portion 259 extending from the rear end 232 of the venous catheter base 23, the extended portion 259 has a thin-wall end 2591 and a handle 2592, and the outer surface of the thin-wall end 2591 of the extended portion 259 is connected with the inner surface of the front portion 51 of the isolating element 5 in a sealed manner.

Figure 5B:
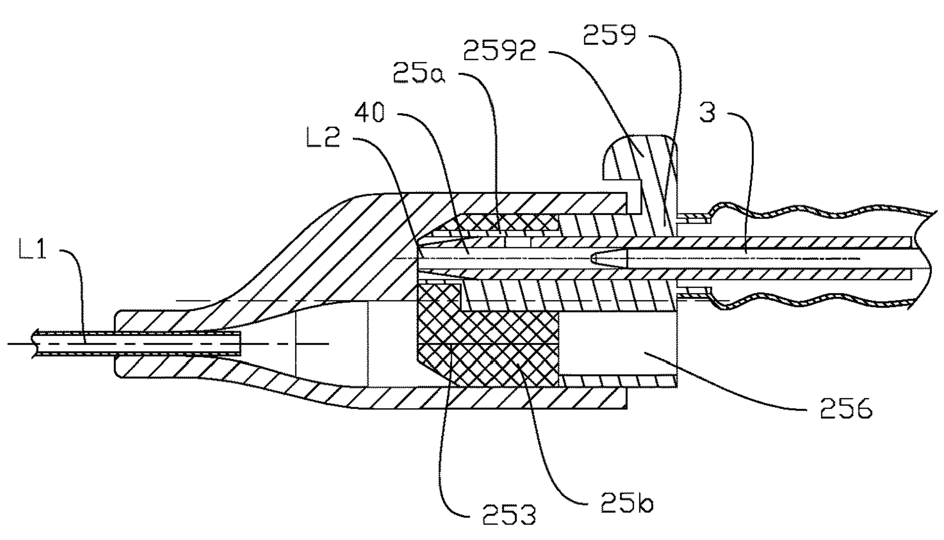
Figure 5C:
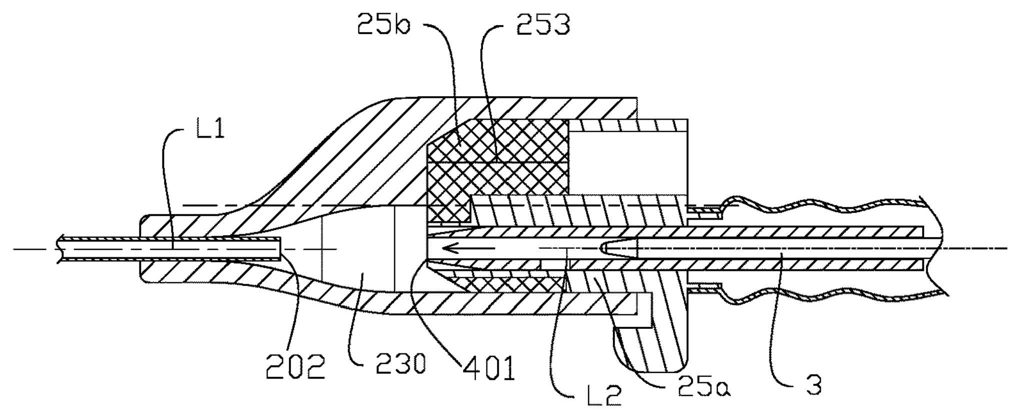

As shown in the section view FIG. 5B, after successful venipuncture, the needle tube 1 is pulled away from the elastic portion 25*b* of the sealer 25, the linear area 253 that the needle tube 1 passes through is closed and isolated from the outer environment, and the concave 256 that previously accommodates the needle tube base 16 is empty. At this time, the external force acts on the extended portion 259 or the handle 2592 of the hard portion 25*a* of the sealer 25, the central axis L2 of the guide passage 40 is moved to the position collinear with the central axis L1 of the venous catheter 2 by rotation and displacement, as shown in FIG. 5C. At this time, the occluding wire 3 can move in the direction indicated by the arrow, that is, the direction coaxial with the central axis L1 of the venous catheter 2.

Figure 5D:
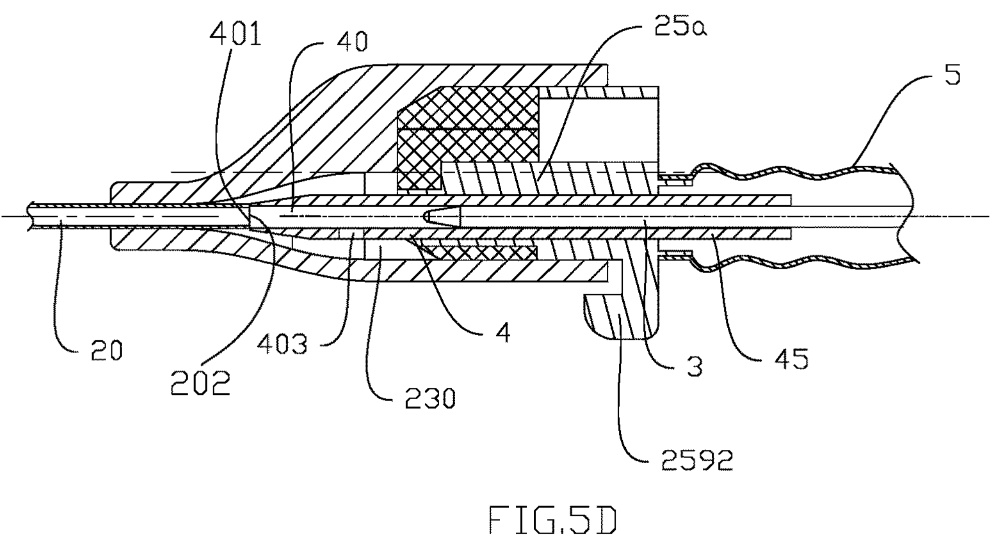

As shown in the sectional view FIG. 5D, in order to ensure that the occluding wire 3 can smoothly enter into the rear-end opening 202 of the venous catheter 2 along the guide passage 40 and avoid possible deflection when passing through the chamber 230 of the venous catheter base 23, the external force is applied to the extension portion 45 of the passage element 4 through the outer surface of the isolating element 5 to drive it to move the axially in an externally-isolated manner, until the front-end opening 401 of the guide passage 40 is connected to the rear-end opening 202 of the venous catheter 2, the occluding wire 3 can smoothly enter the venous catheter lumen 20; the passage element 4 performs translation in the passage of the hard portion 25*a* of the sealer 25, which can be translation under the premise of sealed contact; a plurality of side opening 403 are disposed at the part where the passage element 4 enters into the chamber 230 of the venous catheter base 23. When infusion is needed, the medical liquid can enter into the chamber 230 of the venous catheter base 23 through the infusion collateral (not shown), and then enter into the guide passage 40 and the venous catheter lumen 20 through the openings without returning the passage element 4.

Figure 5E:
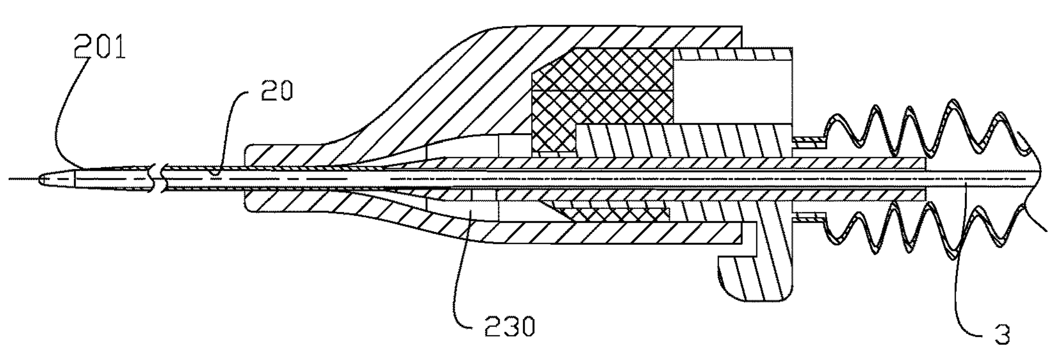

As shown in the section view FIG. 5E, the occluding wire 3 can smoothly enter the venous catheter lumen 20 and occlude the front-end opening 201. The whole travel process of the occluding wire 3 is carried out in the straight tube portion and under continuous guidance.

Embodiment 6

FIGS. 6A, 6B, 6C and 6D show a venous catheter device of Embodiment 6, the biggest difference between Embodiment 6 and Embodiment 2 is that the sealer 25 is provided with a needle tube passage 140. When the needle tube 1 is removed, the needle tube passage 140 will not be closed. Instead, it is connected to a connector 241 of the connecting pipe 24 for medical liquid infusion through a male connector 25*e*, so that the medical liquid in the connecting pipe lumen 240 flows through the needle tube passage 140 into the chamber 230 of the venous catheter base 23, and then into the venous catheter lumen 20.

Figures 6A, 6B, 6C:
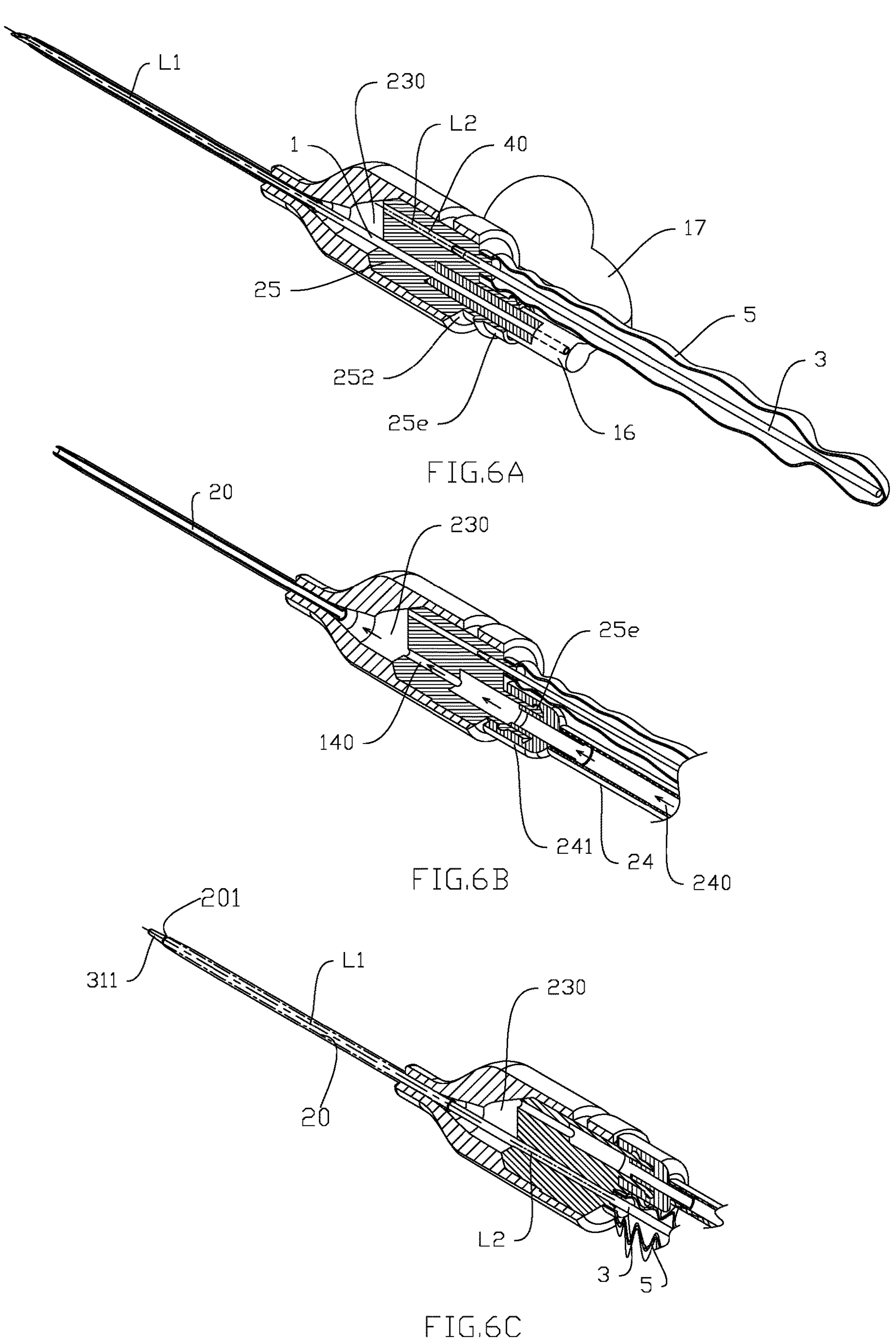
FIGS. 6A, 6B, 6C and 6D are sectional views of the occludable venous catheter device according to Embodiment 6.

FIG. 6A shows that in the initial state, the isolating element 5 is on the top, the needle tube base 16 is on the bottom, the needle tube base handle 17 is extended on the right side, the needle tube 1 is located in the sealer 25 made of hard materials, and the needle base 16 is partially embedded in the male connector 25*e* extending from the rear surface 252 of the sealer 25; the central axis L2 of the straight tube-shaped guide passage 40 is not coaxial but parallel to the central axis L1 of the venous catheter 2.

As shown in FIG. 6B, when the needle tube 1 is removed, the needle tube passage 140 in the sealer 25 appears, and a female connector 241 at the front end of the connecting pipe 24 is connected to the male connector 25*e* in a sealed manner to allow the medical liquid flowing into the venous catheter lumen 20 in the direction of the arrow.

FIG. 6C shows that the central axis L2 of the straight tube-shaped guide passage 40 is collinear with the central axis L1 of the venous catheter 2 after rotation, and the occluding wire 3 occludes the front-end opening 201 of the venous catheter, so that the blood in the venous lumen V0 cannot enter the venous lumen 20, and the medical liquid cannot enter the venous lumen V0; in this embodiment, the guide passage 40 is fully in a straight tube shape, and is formed by the internal passage of the sealer 25 instead of an independent component.

Figures 6D, 7A, 7B:
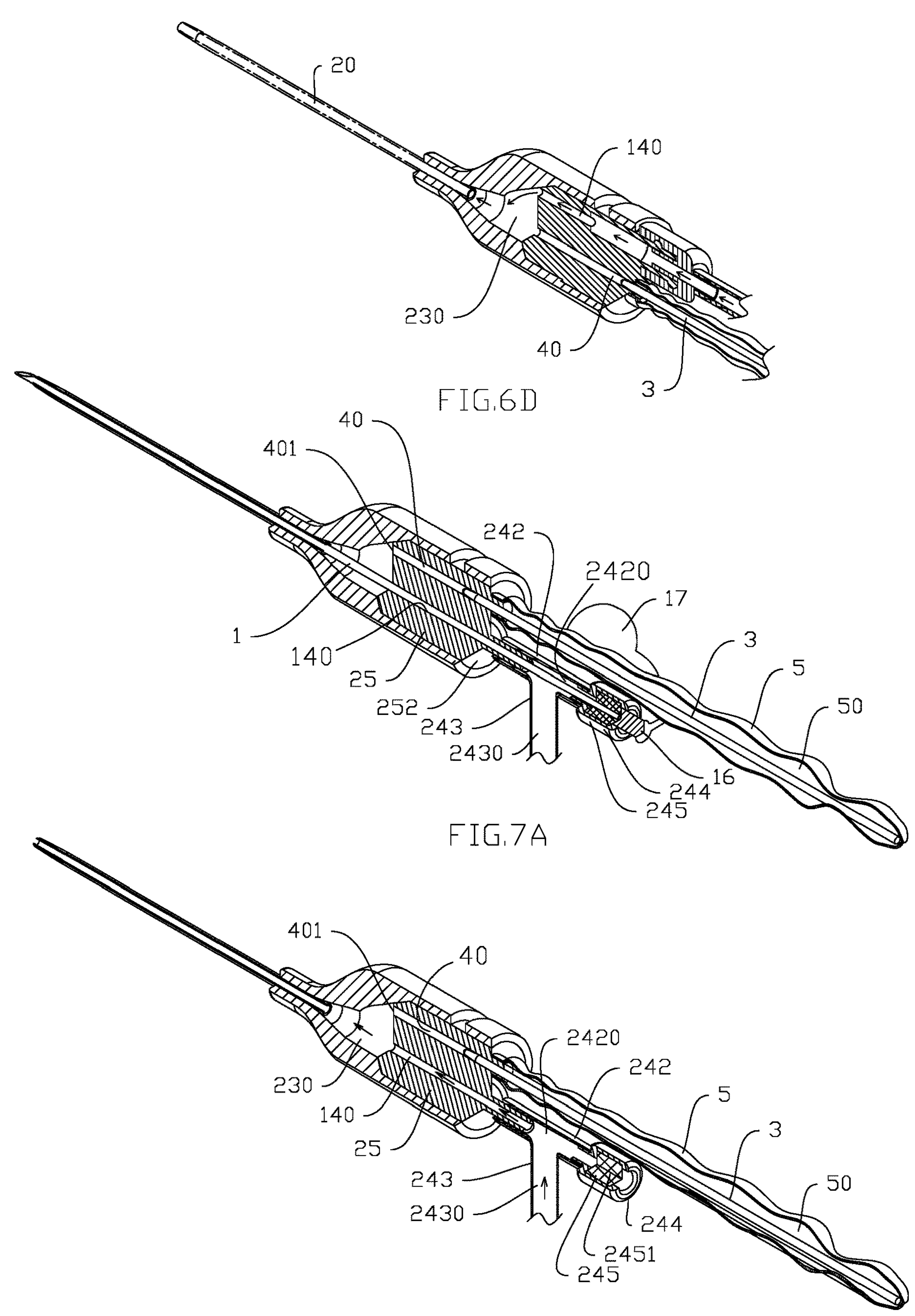
FIGS. 7A, 7B, 7C and 7D are sectional views of the occludable venous catheter device according to Embodiment 7.

FIG. 6D shows that when the occluding wire 3 is retreated into the guide passage 40, the medical liquid can flow into the venous catheter lumen 20 in the direction indicated by the arrow.

Embodiment 7

FIGS. 7A, 7B, 7C and 7D show a venous catheter device of Embodiment 7, the biggest difference from Embodiment 6 is that, the rear end of the sealer 25 is provided with a communicating pipe 242. As shown in FIG. 7A, in the initial state, the communicating pipe 242 is located under the isolating element 5, and has a collateral 243. A collateral lumen 2430 of the communicating pipe 242 can be used to inject medical liquid, the bottom end of the communicating pipe 242 is connected with a joint 244, and an elastic sealing plug 245 is disposed in the joint 244. The needle tube 1 passes through the elastic sealing plug 245, the communicating pipe lumen 2420 and the needle tube passage 140 in the sealer 25, and the needle tube base 16 is connected with the handle 17, which is located outside the joint 244.

As shown in FIG. 7B, after successful venipuncture, the needle tube 1 is removed, and the linear area 2451 through which the needle tube 1 passes on the elastic sealing plug 245 is closed and isolated from the outer environment, the medical liquid can be injected through the collateral lumen 2430 of the communicating pipe 242, the lumen 2420 of the communicating pipe 242 and/or the elastic sealing plug 245 punctured by the infusion needle tube (not shown), and the medical liquid flows into the chamber 230 of the venous catheter base 23 along the direction indicated by the arrow in the figure.

Figures 7C, 7D, 8A:
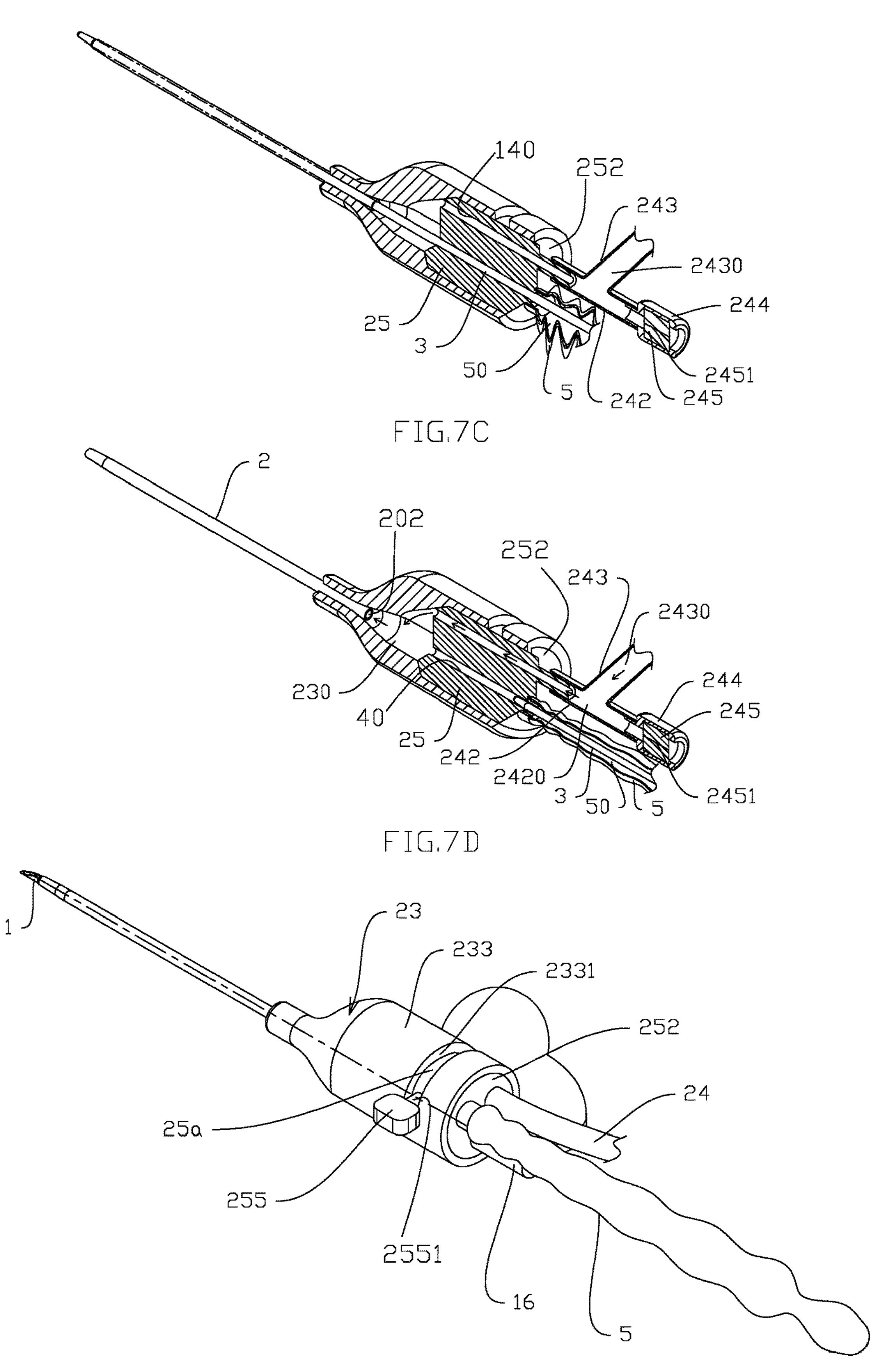
FIGS. 8A, 8B, 8C, 8D and 8E are perspective/sectional views of the occludable venous catheter device according to Embodiment 8.

As shown in FIG. 7C, in the occluded state with no medical liquid injection after rotation in an externally-isolated manner, the communicating pipe 242 is located above the isolating element 5, the bottom end of the communicating pipe 242 is connected with the joint 244 in an externally-isolated manner, and the collateral 243 of the communicating pipe 242 can be connected with the infusion pipeline or occluded by the infusion joint (not shown).

As shown in FIG. 7D, when it is necessary to infuse the medical liquid again, the medical liquid can be injected through the collateral lumen 2430 of the communicating pipe 242 located above the isolating element 5, the lumen 2420 of the communicating pipe 242 and the elastic sealing plug 245 punctured by the infusion needle tube (not shown), and the medical liquid flows into the chamber 230 of the venous catheter base 23 along the direction indicated by the arrow in the figure.

Embodiment 8

FIGS. 8A, 8B, 8C, 8D and 8E show a venous catheter device of Embodiment 8, this embodiment emphasizes that the lumen 240 of the connecting pipe 24 for infusion of medical liquid enters the chamber 230 of the venous catheter base 23 through a infusion passage 250 on the sealer 25.

As shown in FIG. 8A, the needle tube base 16 is located below the isolating element 5, the connecting pipe 24 for medical liquid infusion is connected from the rear surface 252 of the sealer 25, the upper surface 233 of the venous catheter base 23 has the arched window 2331, part of the hard portion 25*a* of the sealer 25 is exposed in the arched window 2331, the hard portion 25*a* of the sealer 25 is connected with the rotation handle 255, and the handle 255 is connected with the hard portion 25*a* of the sealer 25 through the neck 2551.

Figures 8B, 8C, 8D:
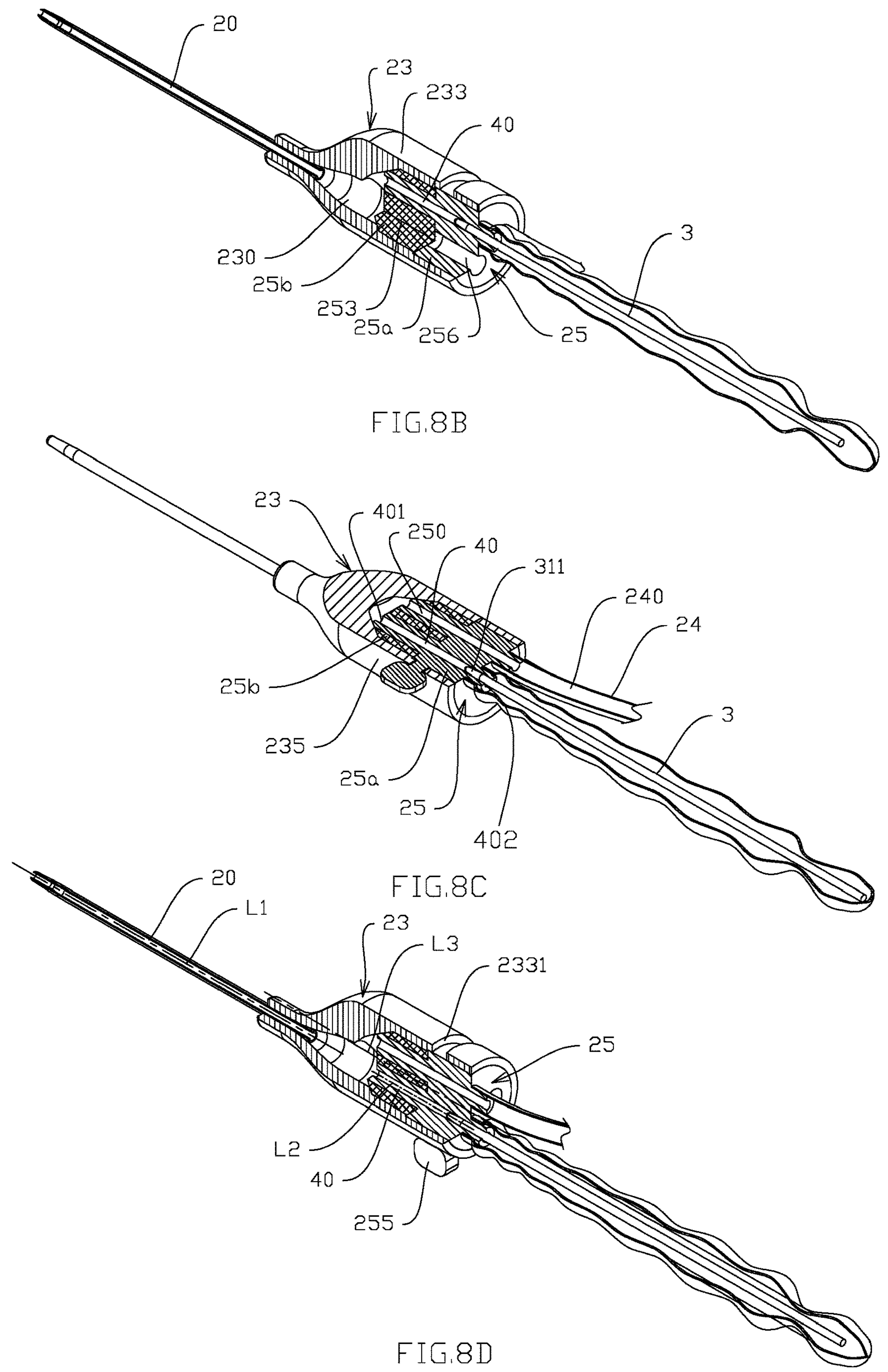

The sectional views FIGS. 8B and 8C from different local views show that the blind end 311 of the front section of the occluding wire 3 is located in the guide passage 40 and adjacent to the rear-end opening 402, the front-end opening 401 of the guide passage 40 is opposite to the inner wall of the venous catheter base 23, and the occluding wire 3 cannot enter the venous catheter lumen 20; the needle tube 1 is removed from the sealer 25, the linear area 253 of the elastic portion 25*b* of the sealer 25 that previously accommodates the needle tube 1 is closed and isolated from the outer environment, and the concave 256 of the hard portion 25*a* accommodating the needle tube base 16 is empty; at this time, the medical liquid can enter the chamber 230 of the venous catheter base 23 from the connecting pipe lumen 240 through the infusion passage 250 on the sealer 25, and then flow into the vein from the venous catheter lumen 20.

FIG. 8D shows that when there is no interference from the needle tube 1 in the venous catheter lumen 20, the rotation handle 255 rotates by 270° from the left side of the guiding structure 2331 to the lower side through the right side, so that the sealer 25 can rotate and displace along the centerline L3 of the venous catheter base 23 as the axis; the central axis L2 of the straight tube-shaped guide passage 40 is collinear with the central axis L1 of the venous catheter 2.

Figure 8E:
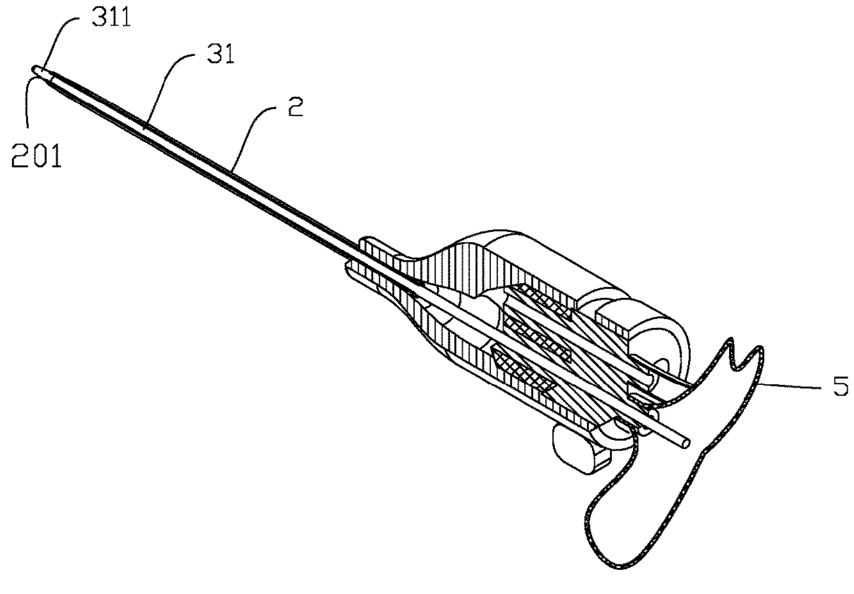

FIG. 8E shows that the blind end 311 of the front section 31 of the occluding wire 3 is tapered and extends from the front-end opening 201 of the venous catheter 2, thus occluding the venous catheter 2, and the whole isolating element 5 is compressed axially and deforms to both sides.

Embodiment 9

Figure 9A:
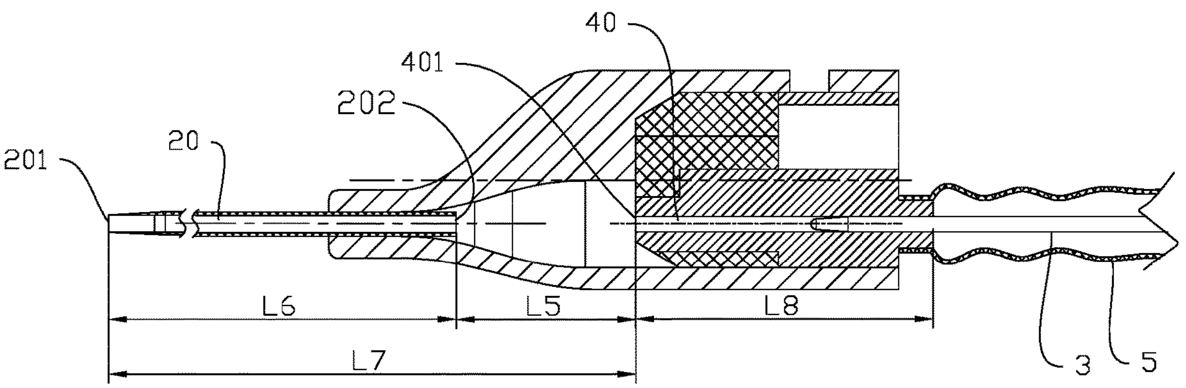
FIGS. 9A and 9B are sectional views of the occludable venous catheter device according to Embodiment 9.
Figure 9B:
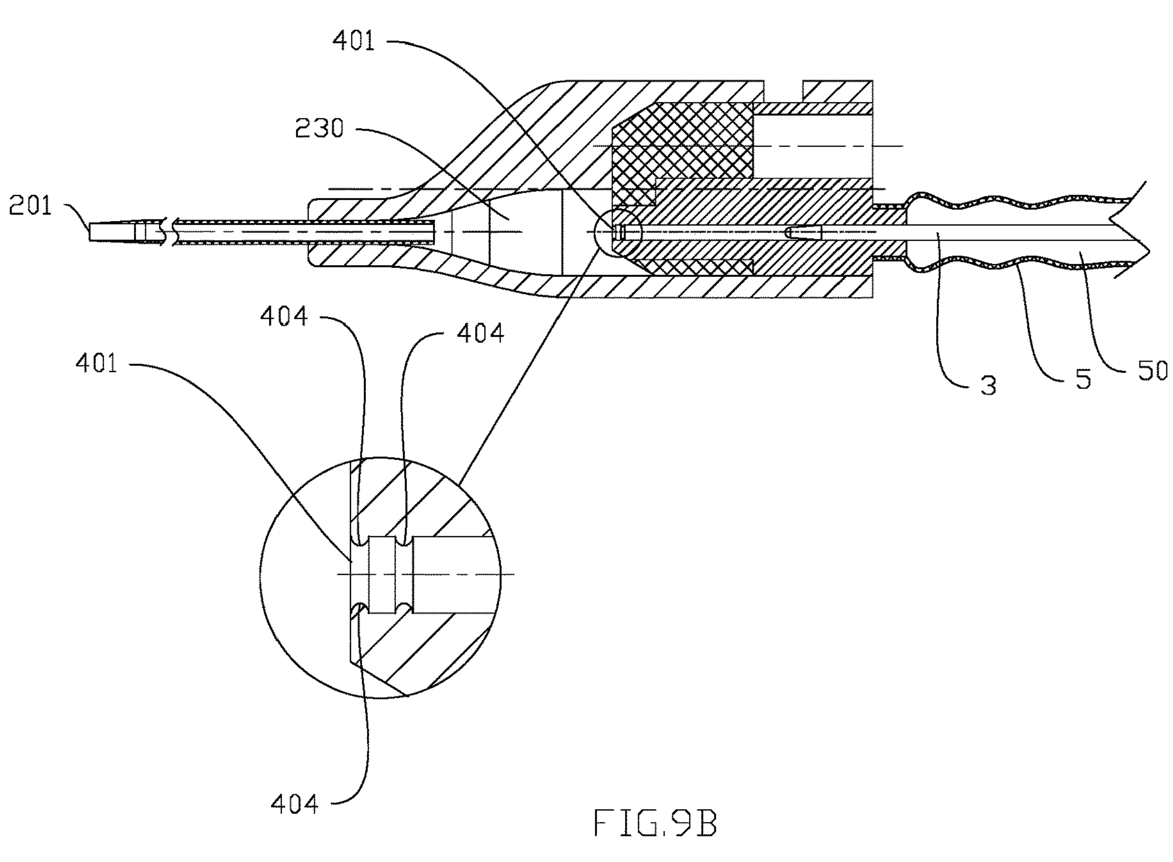

FIGS. 9A and 9B show a venous catheter device of Embodiment 9. As shown in FIG. 9A, the length L8 of the straight tube-shaped guide passage 40 is greater than or equal to the distance L5 between the front-end opening 401 and the rear-end opening 202 of the venous catheter 2. This design can ensure that the occluding wire 3 can move forward coaxially under the constraint of the straight tube-shaped guide passage 40 and smoothly enter the venous catheter lumen 20, and the venous catheter lumen 20 can continue to guide the occluding wire 3.

One solution verified by experiments is that the length L8 of the straight tube-shaped guide passage 40 is greater than or equal to ½ of the length L6 of the venous catheter 2, which can avoid resistance caused by the shaping effect of the bending part of the guide passage 40 on the occluding wire 3 when it enters the venous catheter lumen 20.

A more reliable size preferable solution is that the length L8 of the straight tube-shaped guide passage 40 is greater than or equal to the length L6 of the venous catheter 2, so as to ensure that the occluding wire 3 is not affected by the bending part that may exist in the guide passage 40 during travel.

A more reliable solution is that the length L8 of the straight tube-shaped guide passage 40 is greater than or equal to the distance L7 between the front-end opening 401 thereof and the front-end opening 201 of the venous catheter 2, so that even the occluding wire 3, which is easy to bend, can smoothly enter the venous catheter 20 after being shaped in the straight tube-shaped guide passage 40.

The local enlarged view of FIG. 9B shows that there are two circumferential convexes 404 in the front-end opening 401 of the guide passage 40. The circumferential convexes 404 are in interference fit with the outer surface of the occluding wire 3 to prevent the medical liquid or blood in the chamber 230 of the venous catheter base 23 from entering the chamber 50 of the isolating element from the clearance between them.

Embodiment 10

Figure 10A:
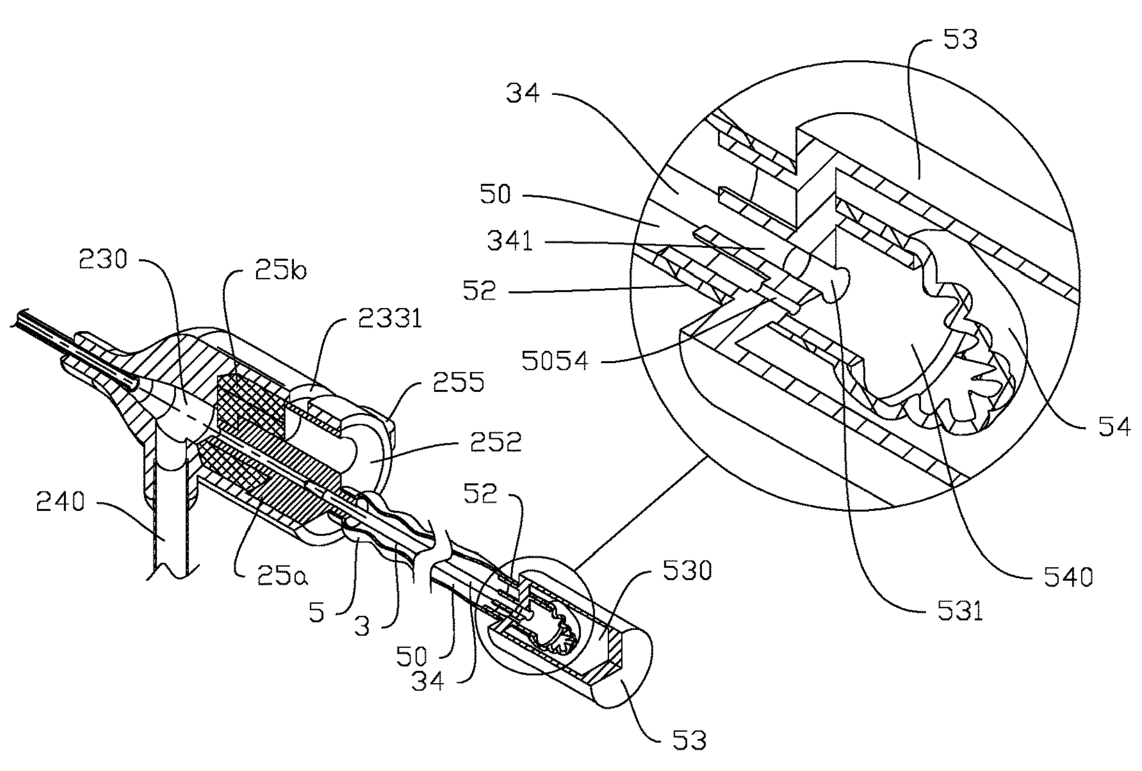
FIGS. 10A and 10B are sectional views of the occludable venous catheter device according to Embodiment 10.
Figure 10B:
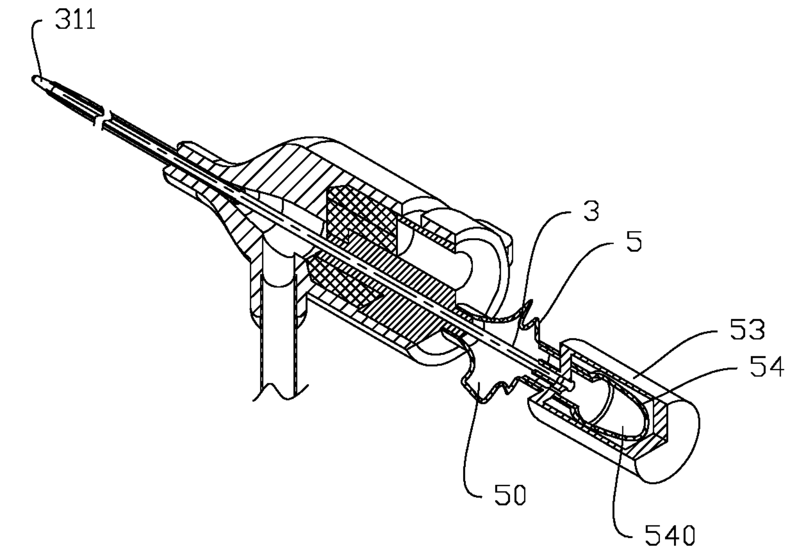

FIGS. 10A and 10B show a venous catheter device of Embodiment 10, the biggest difference from the previous embodiment is that, the back end 52 of the isolating element 5 is connected with a hollow control handle 53, a front-end opening 531 of a control handle lumen 530 is provided with a saccular-shaped fluid transfer element 54 which is easy to expand, and the lumen 540 of the fluid transfer element 54 is connected with the chamber 50 of the isolating element 5 through a connecting hole 5054. In this figure, the fluid transfer element 54 has not expanded, the end 341 of the tail section 34 of the occluding wire 3 is fixed in the front-end opening 531 of the handle lumen 530.

As shown in FIG. 10B, when the finger (not shown) drives the control handle 53 to make the occluding wire 3 move forward, the isolating element 5 is compressed and deforms, and the air in the chamber 50 thereof is pressed into the lumen 540 of the expanded fluid transfer element 54, so as to avoid the resistance caused by air compression to interfere with the occluding wire 3 moving forward; the control handle 53 can be flat, columnar, ellipsoidal, etc.

Embodiment 11

Figure 11:
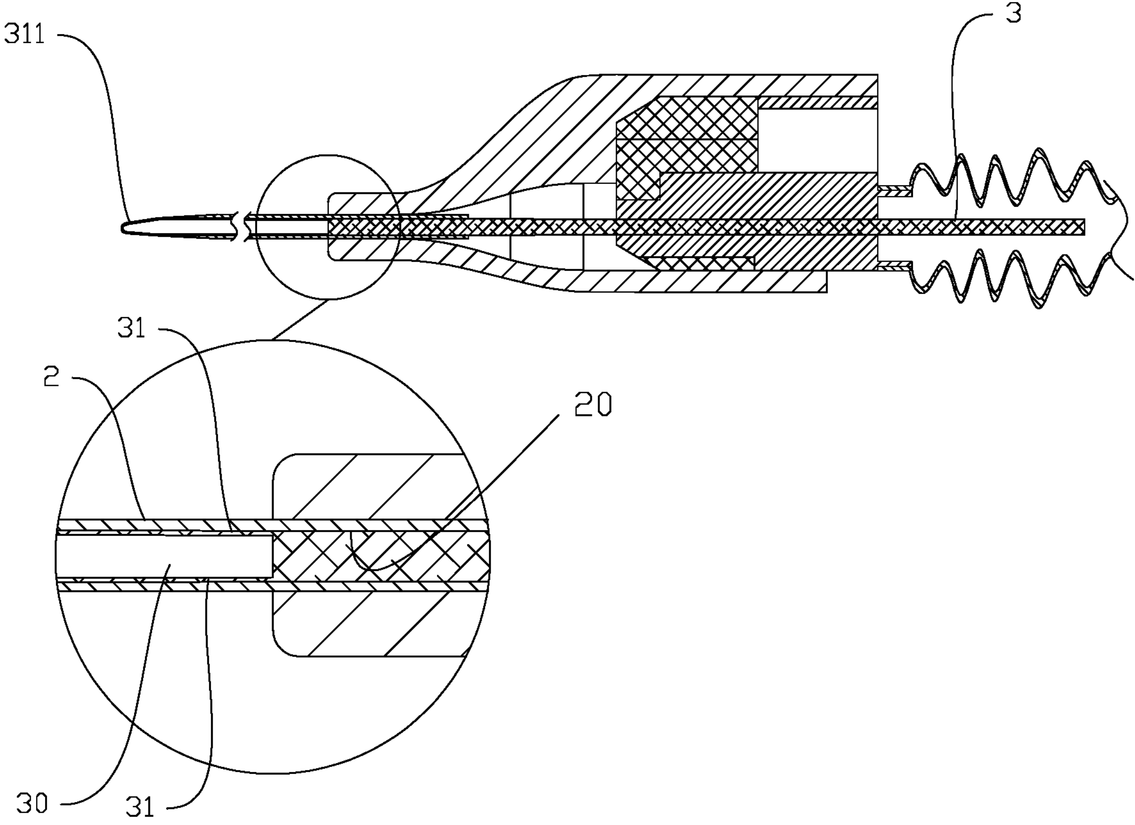
FIG. 11 is a sectional view of the occludable venous catheter device according to Embodiment 11.

FIG. 11 shows a venous catheter device of Embodiment 11, the biggest difference from the previous embodiment is that, at least the front section 31 of the occluding wire 3 is hollow, thus forming an occluding wire lumen 30, and the blind end 311 at the top of the occluding wire 3; because the front section 31 of the occluding wire 3 enters the venous catheter lumen 20 in the occluded state, the internal hollow part can greatly reduce the deflection of the front section, so as to avoid the increase of the overall deflection after being overlapped with the venous catheter 2, and reduce the possible extrusion damage of the venous catheter 2 to the venous wall V during the occlusion process.

A heat generating element can be arranged in the front section 31 of the occluding wire 3 or the occluding wire 3 as a whole (not shown). The heat generating element can be a metal heating wire or an element which generates heat by non-direct contact electromagnetic induction; in the occluded state, the heat generating element makes the temperature of the venous catheter 2, especially the front end 211, in the venous lumen V0 equal to or higher than the temperature of the blood in the vein, so as to effectively avoid the blood coagulation on the venous catheter 2.

Embodiment 12

Figures 12A, 12B:
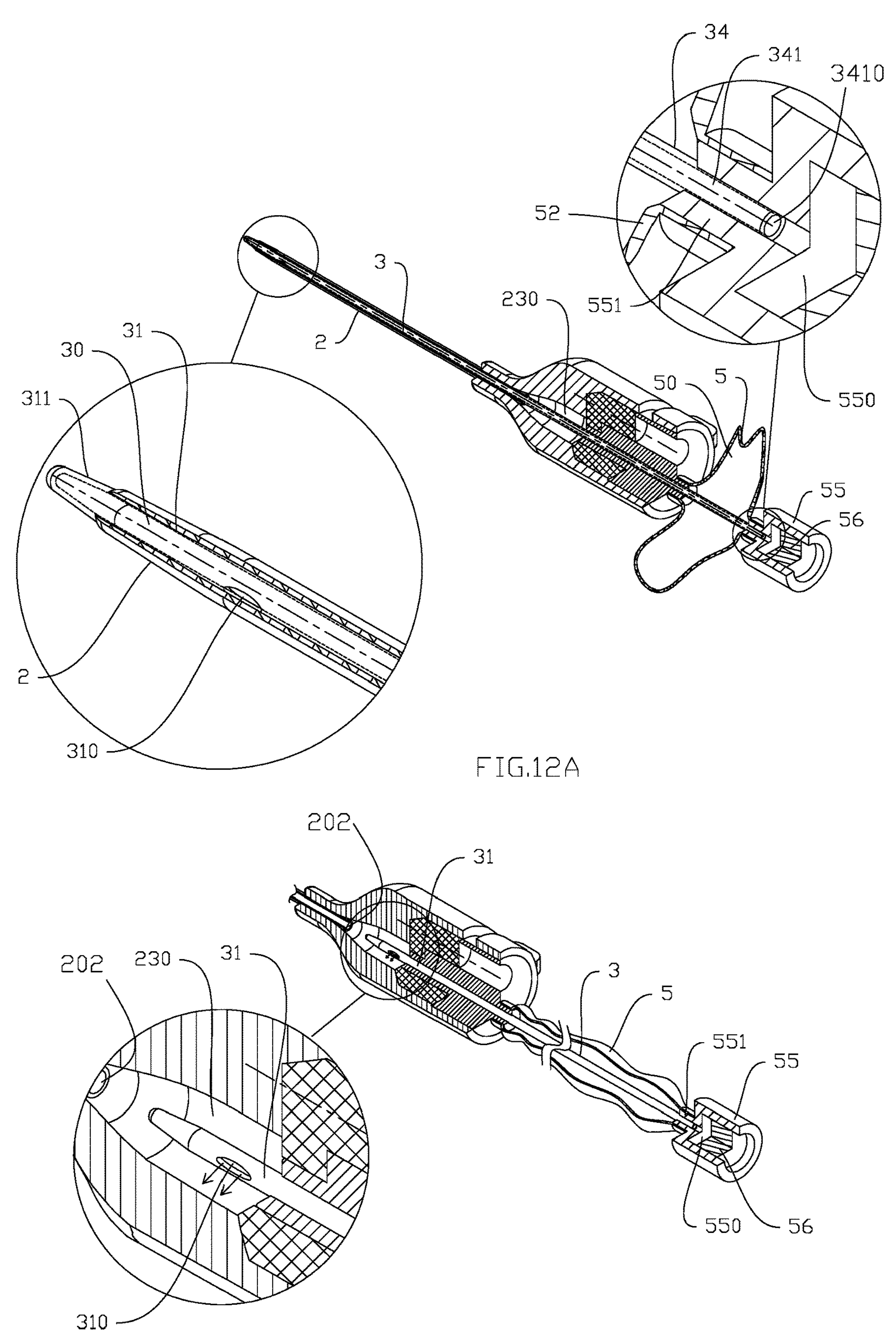
FIGS. 12A and 12B are sectional views of the occludable venous catheter device according to Embodiment 12.

FIGS. 12A and 12B show a venous catheter device of Embodiment 12. The solution in this embodiment is that the occluding wire lumen 30 can be used as a passage for medical liquid infusion.

As shown in FIG. 12A, the occluding wire 3 is hallow in whole, forming the occluding wire lumen 30, with an opening 3410 at an end 341 of the occluding wire 3 and the blind end 311 at the top of the occluding wire 3, and at least one side hole 310 in the front section 31; the end opening 3410 of the occluding wire 3 is communicated with a lumen 550 of a hollow handle 55; a front end 551 of the control handle 55 is relatively thin, the inner part of the front end 551 is hollow and sleeved with an occluding wire tail section 34, and the lumen 550 of the control handle 55 is filled with an elastic sealing plug 56. This figure shows that in the occluded state after the needle tube 1 is removed, the venous blood cannot flow back to the chamber 230 of the venous catheter base 23; the enlarged image on the left shows that the side hole 310 of the front section of the occluding wire 3 is close to the inner wall of the venous catheter 2.

As shown in FIG. 12B, when it is necessary to infuse medical liquid, the control handle 55 is pulled to extend the isolating element 5, and the front section 31 of the occluding wire 3 is removed from the rear-end opening 202 of the venous catheter. At this time, the external needle tube 1 is inserted into the elastic sealing plug 56 of the handle lumen 550 to infuse the medical liquid (not shown), and the medical liquid enters the occluding wire lumen 30 through the handle lumen 550. As shown by the arrow in the figure, the liquid flows into the chamber 230 of the venous catheter base 23 from the side hole 310 of the front section of the occluding wire 3.

Embodiment 13

Figure 13A:
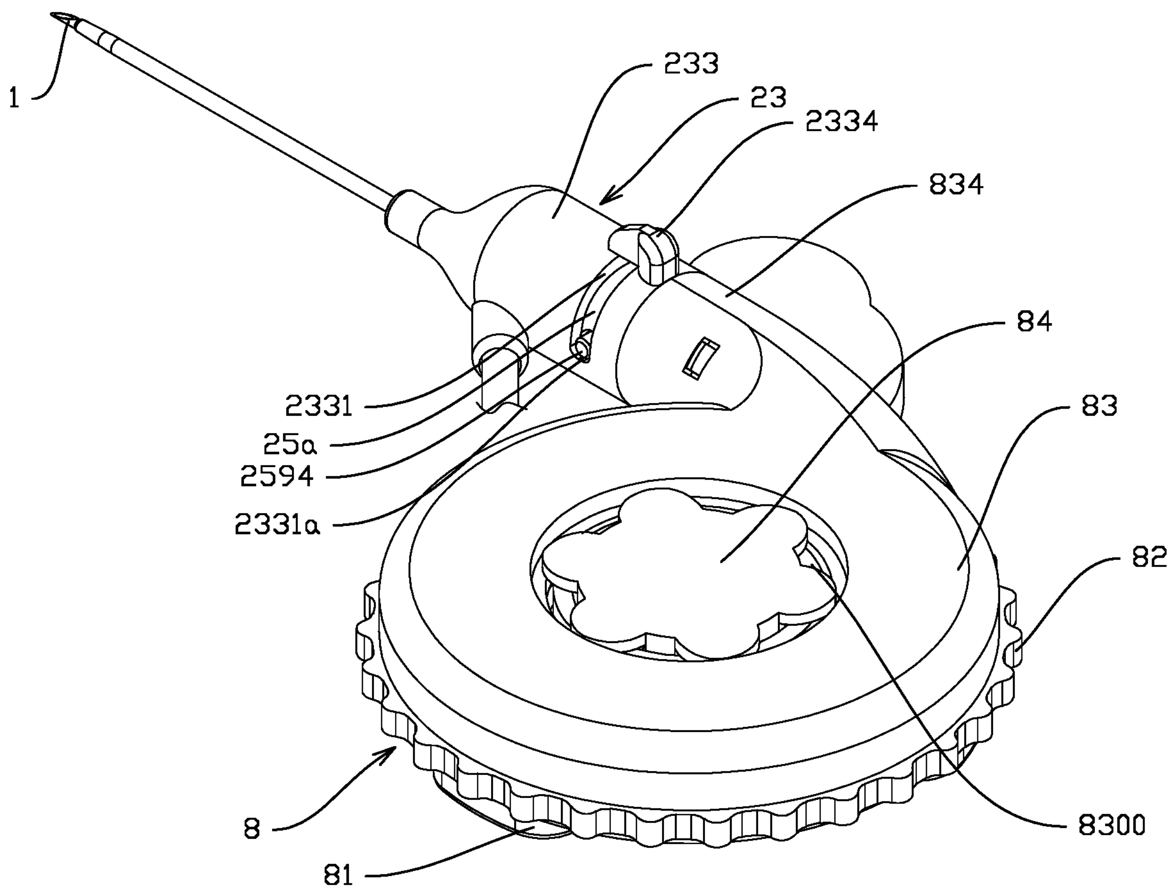
FIGS. 13A, 13B, 13C, 13D, 13E, 13F, 13G, 13H, 13I, 13J, 13K, 13L, 13M and 13N are perspective/sectional views of the occludable venous catheter device according to Embodiment 13.
Figure 13B:
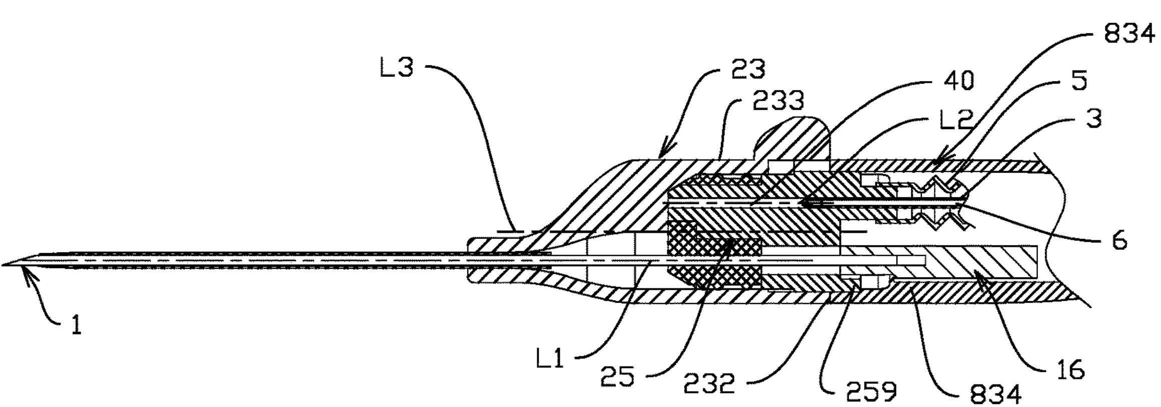
Figure 13C:
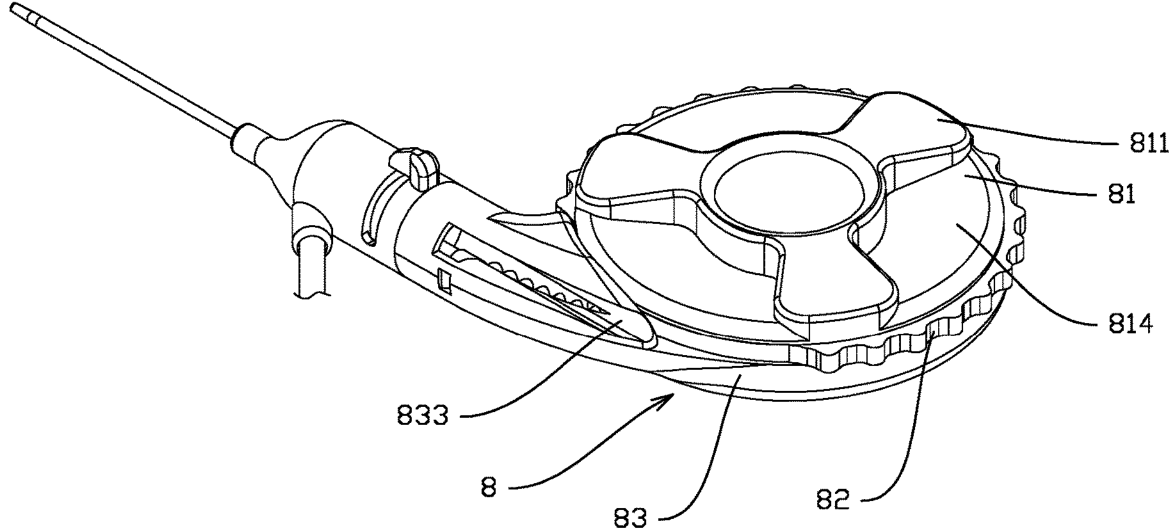
Figure 13D:
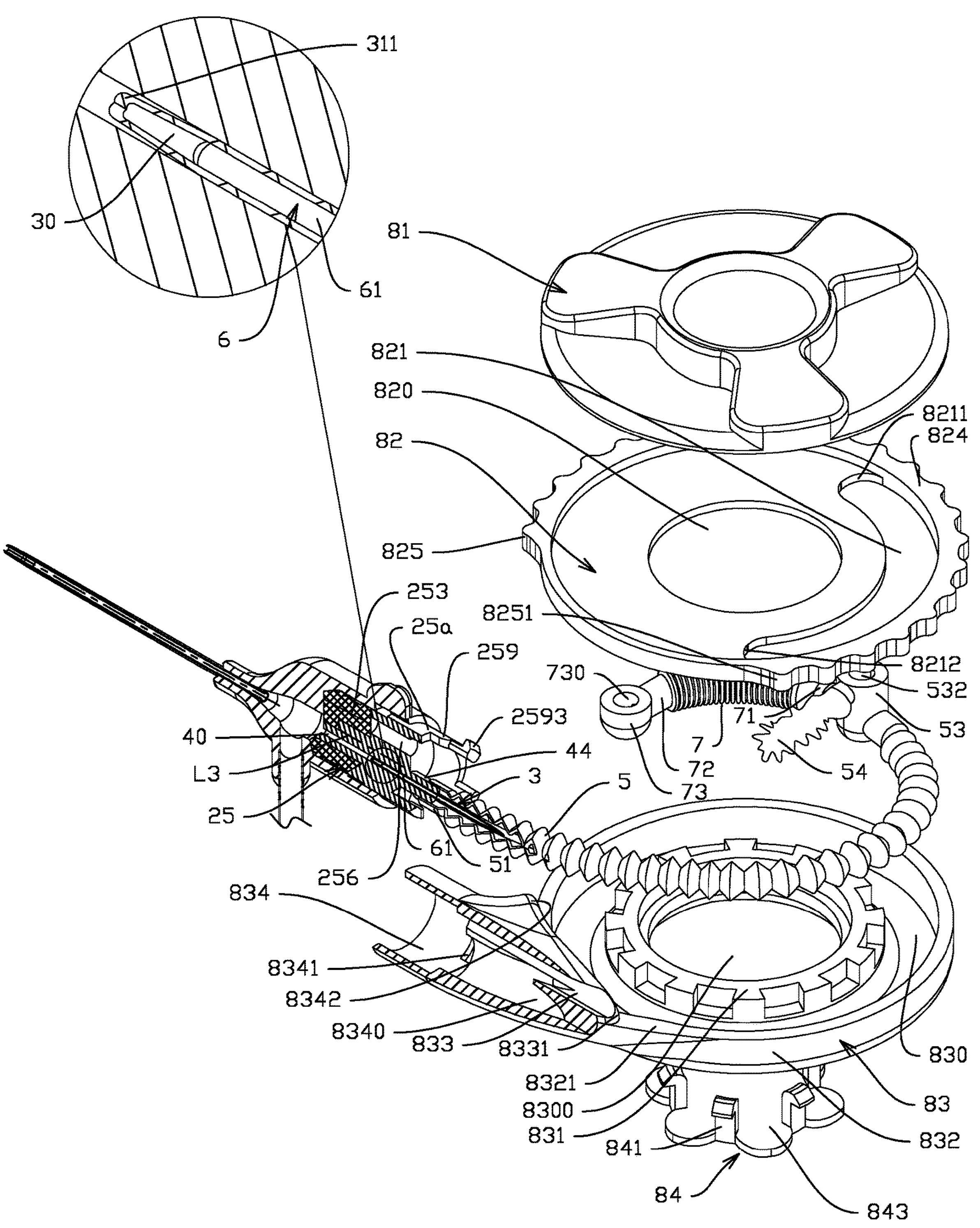
Figure 13E:
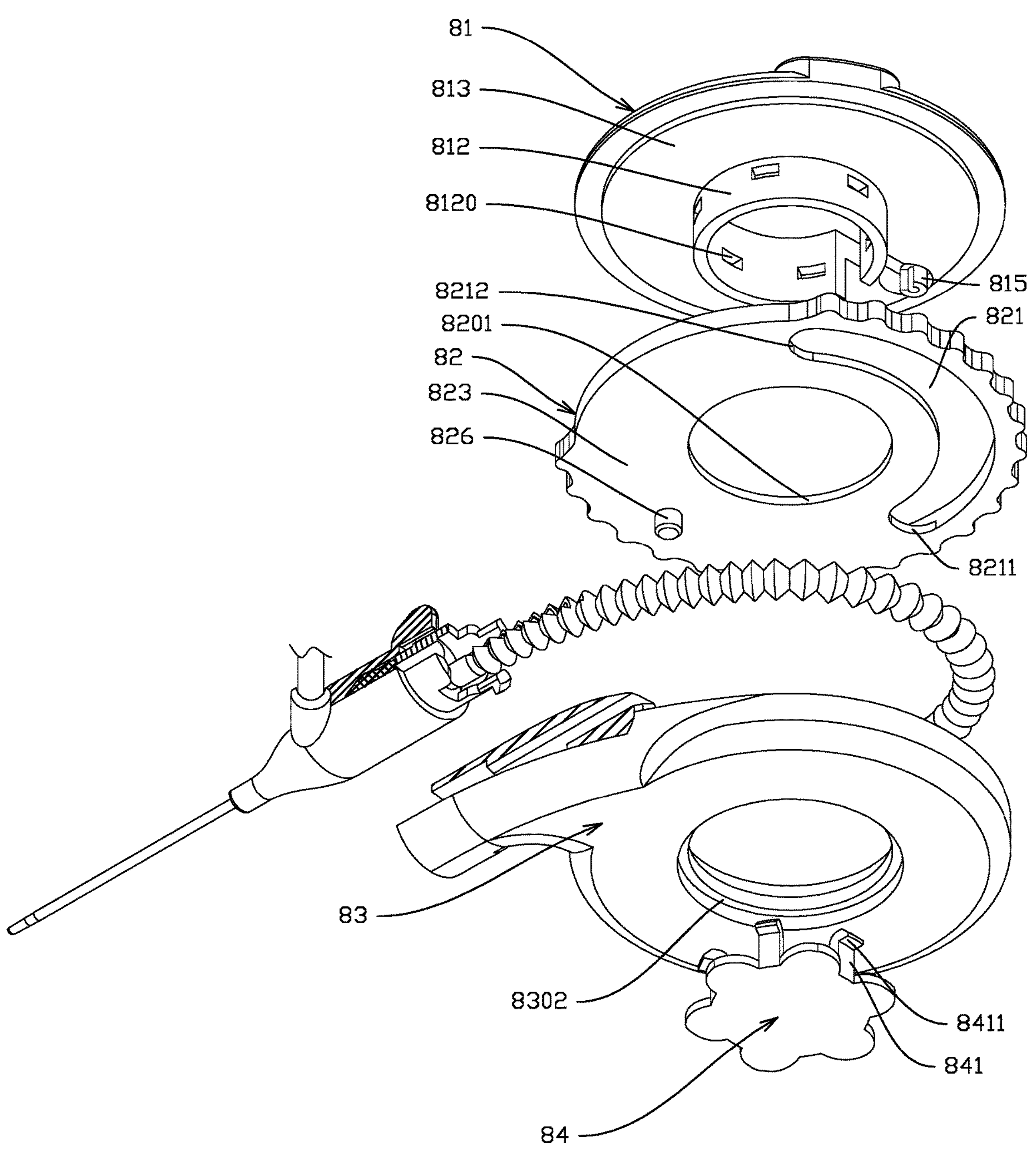
Figure 13F:
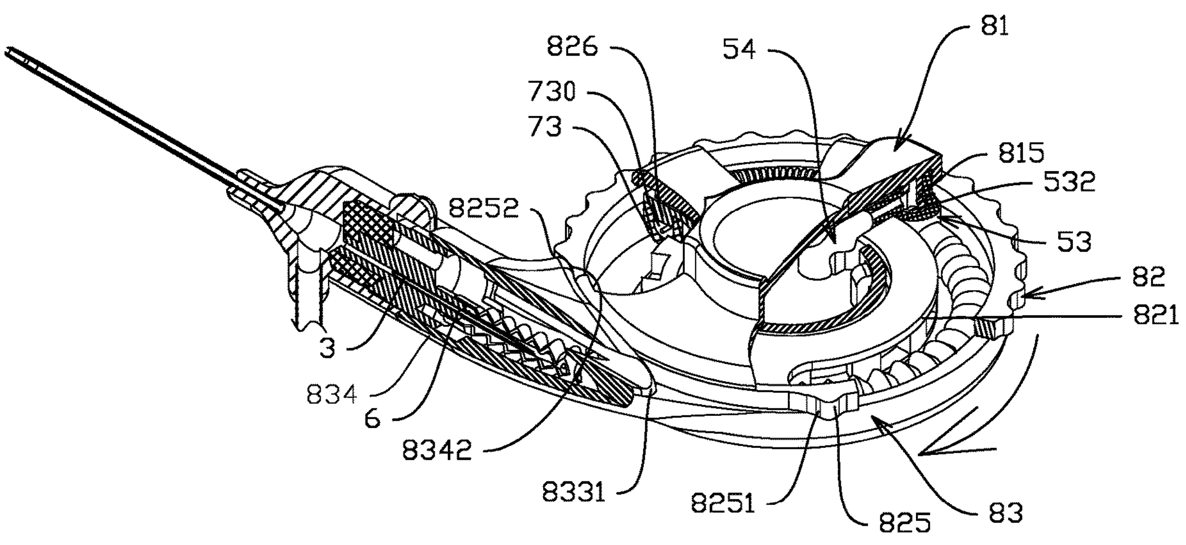
Figure 13G:
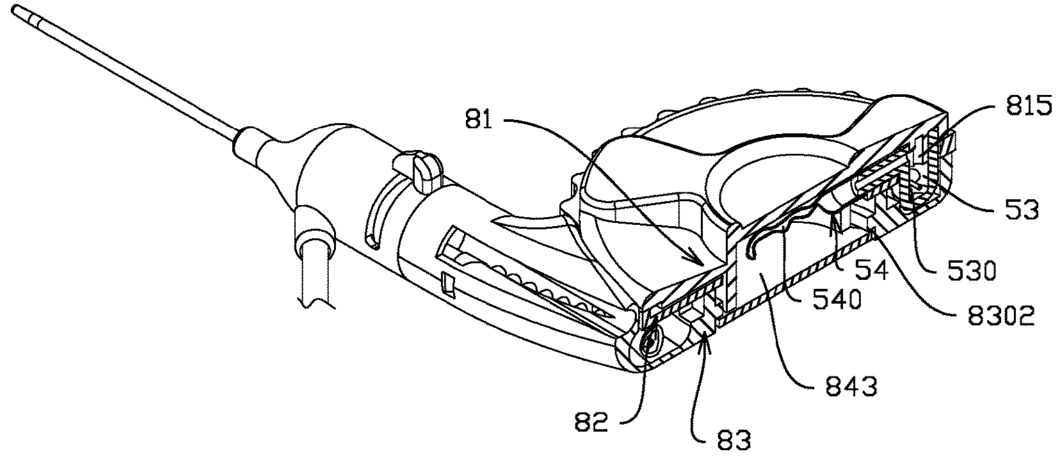
Figure 13H:
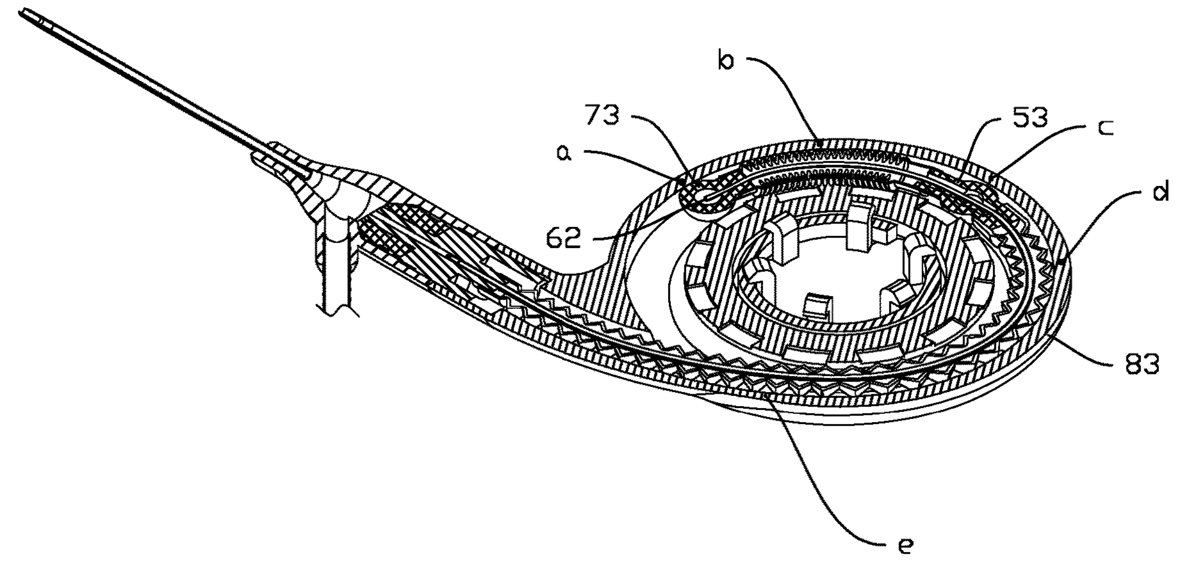
Figure 13I:
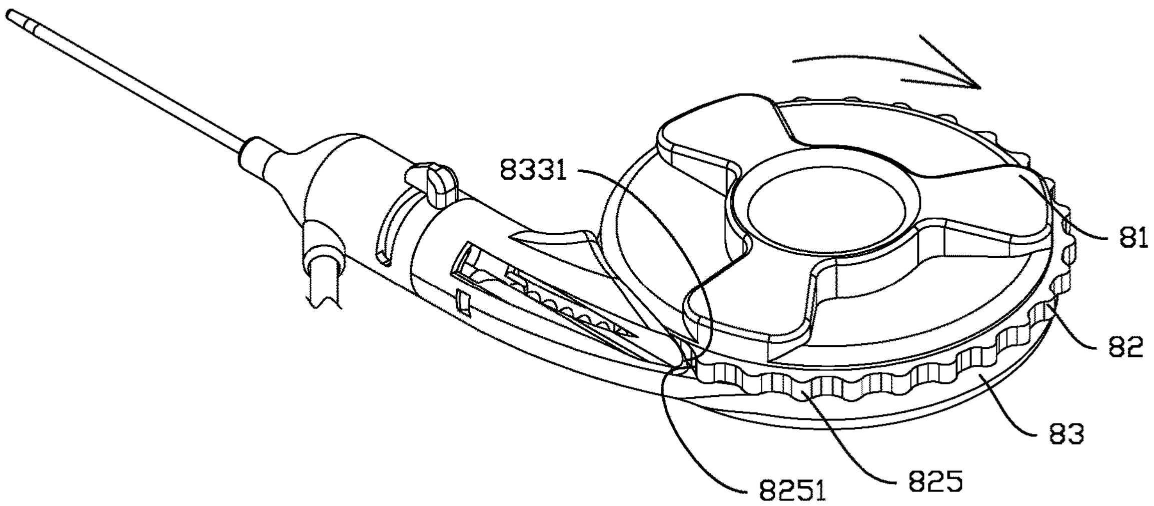
Figure 13J:
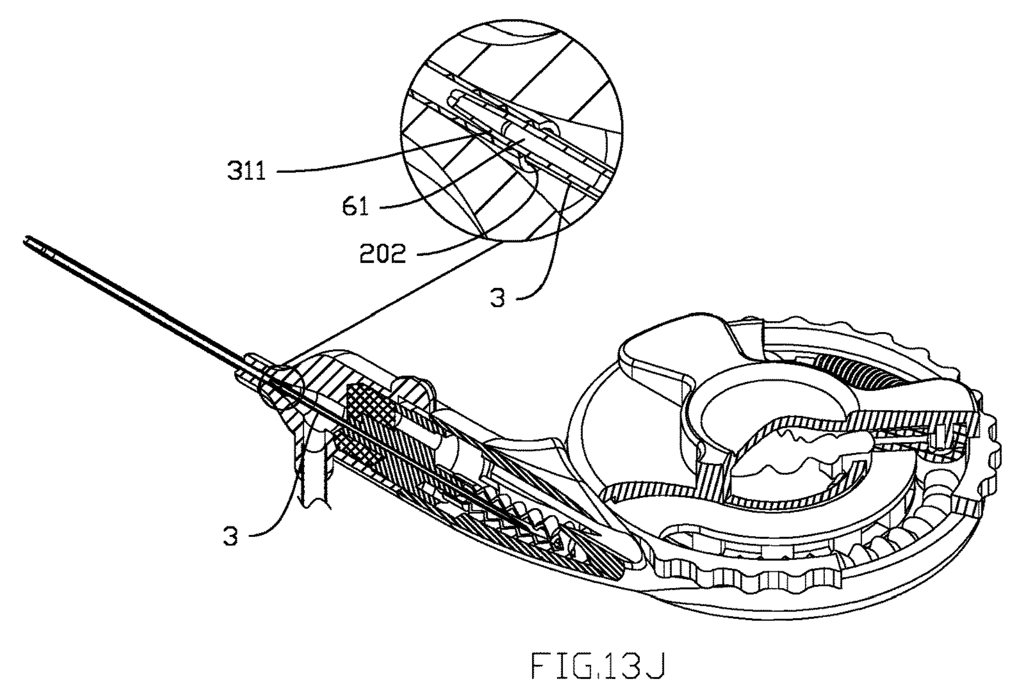
Figure 13K:
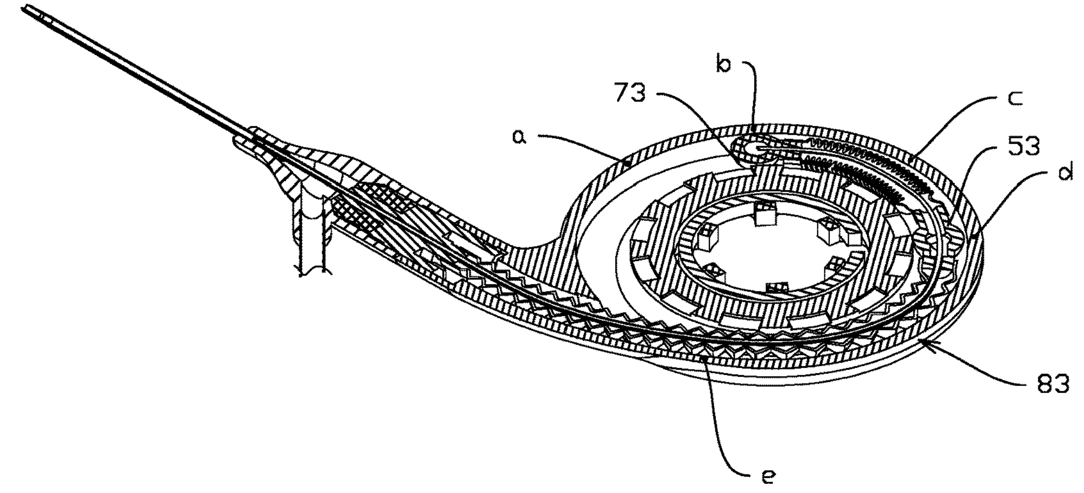
Figure 13L:
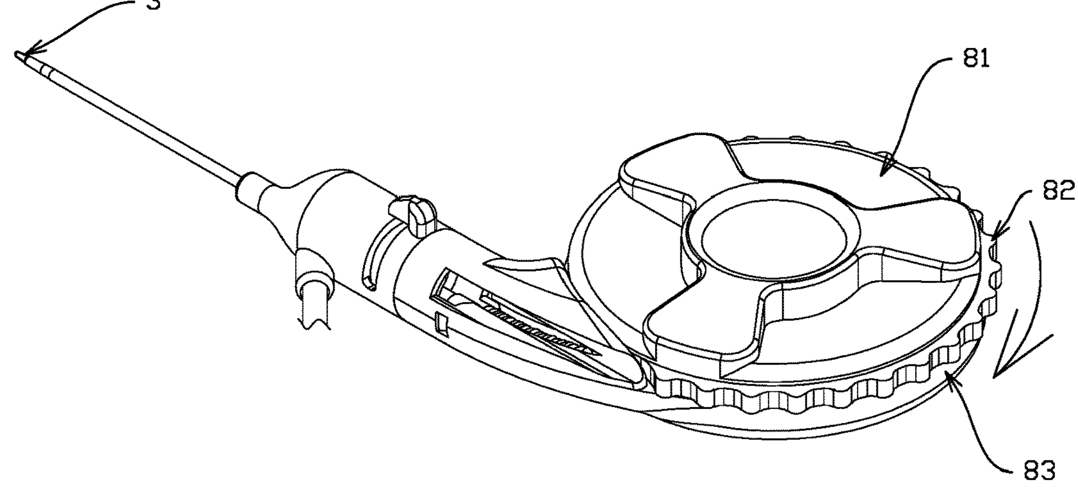
Figure 13M:
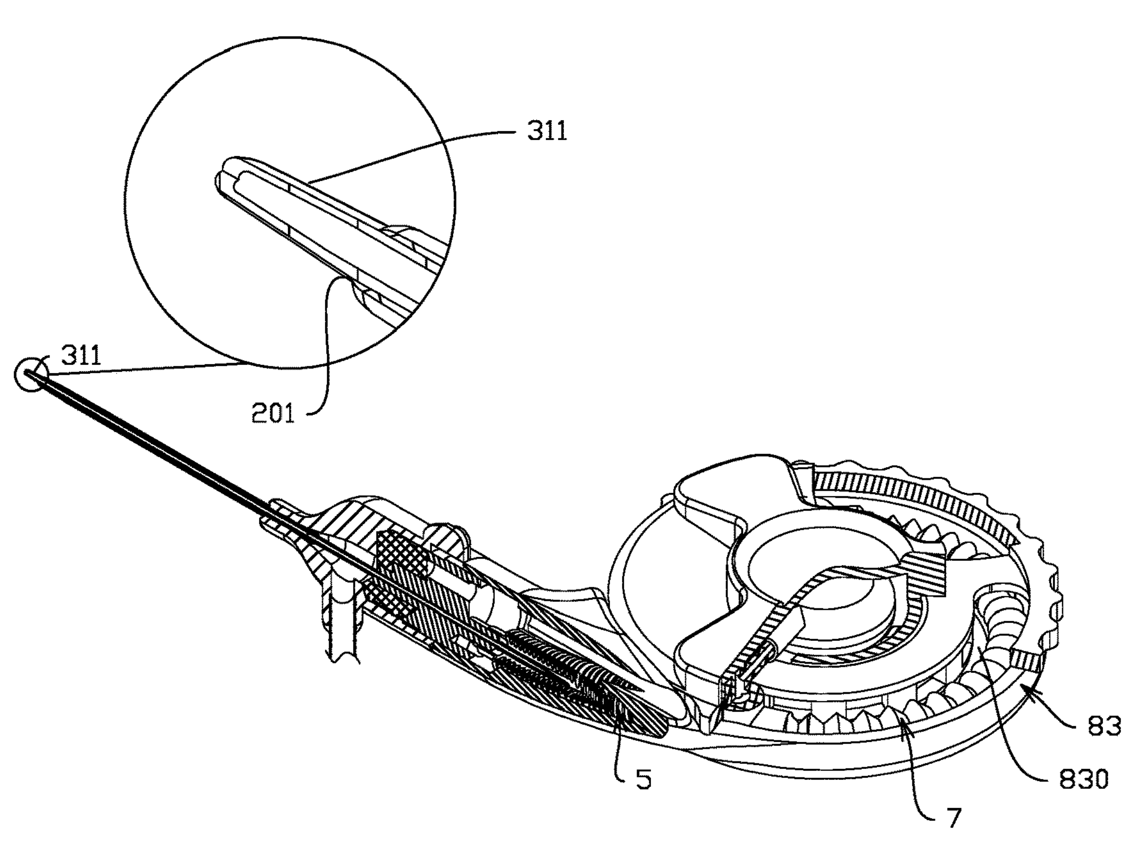
Figure 13N:
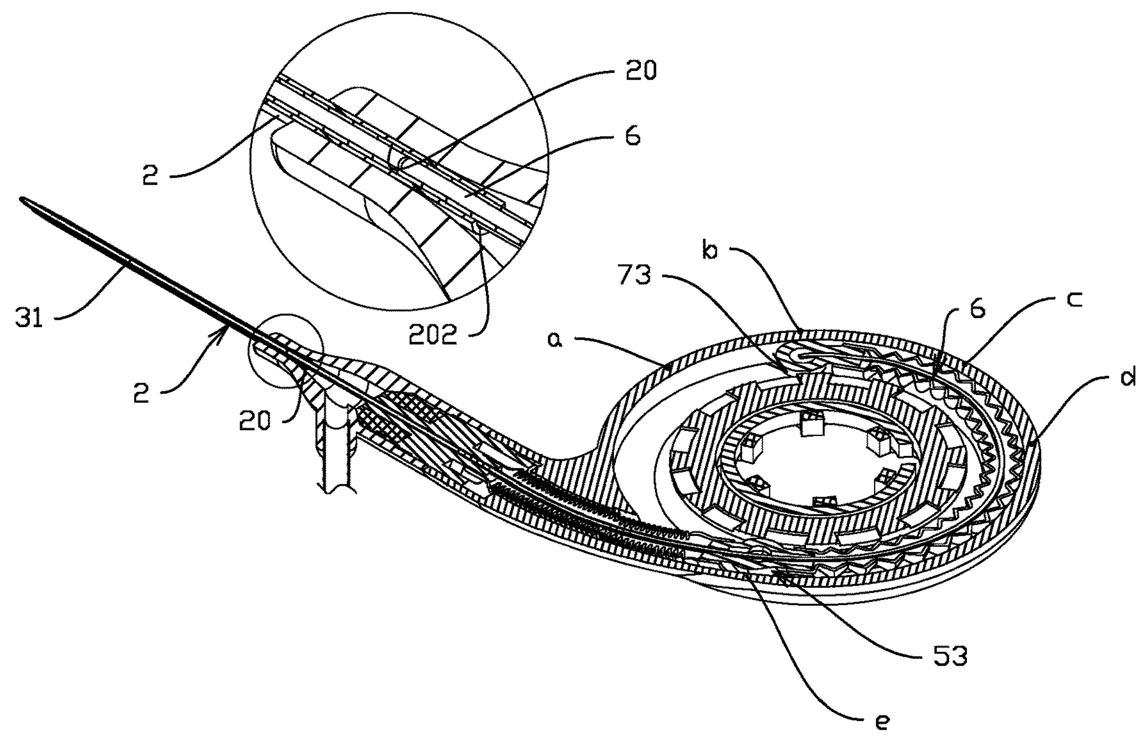

FIG. 13A-13N show a venous catheter device of Embodiment 13. The solution of this embodiment is that the central axis L2 of the guide passage 40 is adjusted to be collinear with the central axis L1 of the venous catheter 2 through rotation has been described in detail above. The biggest difference is that the occluding wire 3 and the isolating element 5 are externally sleeved with a housing assembly 8 which is convenient for driving, and the components of the housing assembly 8 can accurately control the movement of the occluding wire 3 and the pushing guide wire 6 therein.

FIGS. 13A and 13B show that the structure of venous catheter base 23 is roughly the same as that in Embodiment 2. In the initial state, the central axis L2 of the straight tube-shaped guide passage 40 is not coaxial but parallel to the central axis L1 of the venous catheter 2. The needle tube base 16 is located below the isolating element 5. The upper surface 233 of venous catheter base 23 has the guiding structure 2331, and part of the hard portion 25*a* of the sealer 25 is exposed in the guiding structure 2331. The difference is that the rear end of the hard portion 25*a* of the sealer 25 has an extended portion 259 extending from the rear surface 232 of the venous catheter base 23, and the extended portion 259 is sleeved with a connecting portion 834 of a lower housing portion 83 of the housing assembly 8; the housing assembly 8 is disc-shaped and is composed of the lower housing portion 83, a middle housing portion 82, an upper housing portion 81 and an assembly plate 84; in the initial state as shown in FIGS. 13A and 13B, the lower housing portion 83 is on the top, the middle housing portion 82 is in the middle, the upper housing portion 81 is on the bottom, and the assembly plate 84 passes through a central cave 8300 of the lower housing portion 83; in order to increase the stability, the central position of the guiding structure 2331 has a bridge-shaped stiffener 2334 extending upward and crossing forward and backward longitudinally, the hard portion 25*a* of the sealer has a cylindrical limiting convex 2594 which is not exposed in the guiding structure 2331, and the cylindrical limiting convex 2594 contacts a left edge 2331*a* of the guiding structure 2331; when the limiting convex 2594 contacts the right edge of the guiding structure 2331, the central axis L2 of the guide passage 40 is coaxial with the central axis L1 of the venous catheter 2.

As shown in FIG. 13D, the extended portion 259 of the hard portion 25*a* of the sealer 25 has a plurality of clips 2593, which are embedded in a rectangular assembly hole 8341 on the connecting portion 834 of lower housing portion 83, so as to connect the two as a whole; when the needle tube 1 is removed, the finger holds the main body of the lower housing portion 83 and other parts of the housing assembly 8 connected therewith to rotate, which can drive the sealer 25 to rotate half a circle synchronously along the L3 axis, changing from the initial state in FIG. 13A to the coaxial state in FIG. 13C. At this time, the lower housing portion 83 is in the lower position, the upper housing portion 81 is in the upper position, and an upper surface 814 of the upper housing portion 81 has three blade-shaped convexes 811; FIG. 13C also shows an oblique groove 833 on the left side of the lower shell housing portion 83, in which the needle tube base 16 is partially located before being removed.

FIG. 13D also shows that after the needle tube 1 is removed, the linear area 253 is closed and isolated from the outer environment, the concave 256 of the needle tube base 16 on the sealer 25 is empty, and the hollow occluding wire lumen 30 is provided with the pushing guide wire 6. The local enlarged part shows that there is a certain clearance between a front end 61 of the pushing guide wire 6 and the inner side of the blind end 311 of the front section of the occluding wire 3, and of course, they can completely contact with each other; the pushing guide wire 6 can be made of titanium alloy, stainless steel and other metal materials or hard PET, PA and other resins. The arrangement of pushing guide wire 6 increases the strength of hollow occluding wire 3 to facilitate its forward movement.

Further, the extended section 44 extends from the rear end of the hard portion 25*a* of the sealer 25 forming the guide passage 40, the outer surface of the extended section 44 is connected in a sealed manner with the inner surface of the front-end opening part 51 of the corrugated tubular isolating element 5, the end of the corrugated tubular isolating element 5 is connected with the control handle 53, the upper surface of the handle 53 has an assembly hole 532, and one side of the handle 53 is connected with a fluid transfer element 54 which is easy to expand and deform; the rear end of the control handle 53 is connected with a proximal part 71 of a pushing guide wire isolating element 7, a distal part 72 thereof stops at a pushing guide wire control handle 73, and the upper surface of the control handle 73 has an assembly hole 730; between an outer ring rib 832 and an inner ring rib 831 of the lower housing portion 83 is a ring-shaped accommodating groove 830, and the isolating element 5 and the pushing guide wire isolating element 7 are assembled to the accommodating groove 830 and the connecting portion lumen 8340 communicated therewith. The design of a plurality of recesses in the ring rib 831 of the lower housing portion 83 can reduce the weight of the material and the production cost.

As shown in FIGS. 13D and 13E, a central cave 820 of the middle housing portion 82 is sleeved on an inner ring rib 812 of the upper housing portion 81, and the outer surface of the inner ring rib 812 is adjacent to a central cavity cave 8201 of the middle housing portion 82, and the adjacency is relatively mobile contact or close distance; the middle housing portion 82 has an arc-shaped window 821, and the control handle 53 is sleeved in the arc-shaped window 821; a lower surface 813 of the upper housing portion 81 has an embedding column 815, which is embedded into an assembly hole 532 of the upper surface of the control handle 53 through the arc-shaped window 821 of the middle housing portion 82, so as to connect the upper housing portion 81 with the isolating element 5 and the occluding wire 3; the lower surface 823 of the middle housing portion 82 has an embedding column 826, which is embedded in the assembly hole 730 on the upper surface of the control handle 73, so that the middle housing portion 82 is connected with the pushing guide wire isolating element 7 and the pushing guide wire 6.

Further, the lower surface 823 of the middle housing portion 82 is adjacent to the upper surface 8321 of the outer ring rib 832 of the lower housing portion 83, and the lower surface 813 of the upper housing portion 81 is adjacent to the upper surface 824 of the middle housing portion 82; the upper surface 843 of the assembly plate 84 is connected with the lower surface 8302 of the annular convex of the central cave 8300 of the lower housing portion 83 (FIG. 13G). The assembly plate 84 has a plurality of vertically upward clips 841, and the clips 841 of the assembly plate 84 pass through the central cave 8300 of the lower housing portion 83 and the central cavity 820 of the middle housing portion 82, finally an outward convex portion 8411 of the clips of the assembly plate 84 are respectively embedded in a plurality of corresponding lateral assembly holes 8120 on the ring rib 812 of the lower surface 813 of the upper housing portion 81, so as to assemble the housing assembly 8 as a whole; the middle housing portion 82 and the upper housing portion 81 can rotate relative to the lower housing portion 83, and the middle housing portion 82 and the upper housing portion 81 can also rotate relative to each other; apparently, the upper housing portion 81 is connected with the assembly plate 84 and rotates synchronously; when the upper housing portion 81 is made to rotate to drive the control handle 53 located in the arc-shaped window 821 to rotate, the rotation range of the control handle 53 is limited between a proximal edge 8212 and a distal edge 8211 of the arc-shaped window 821; in order to facilitate finger operation, the outer edge of the middle housing portion 82 has a plurality of dentate convexes 825, and the middle housing portion 82 stops rotating when a front end 8251 of the proximal dentate convexes 825 contacts an oblique groove convex 8331 of the lower housing portion 83.

As shown in the local section view of FIG. 13F, when the needle tube 1 is removed and the central axis L2 of the guide passage 40 and the central axis L1 of the venous catheter 2 are rotated to be coaxial, an embedding column 815 of the upper housing portion 81 is embedded into the assembly hole 532 of the upper surface of the control handle 53 through the arc-shaped window 821 of the middle housing portion 82 (see FIG. 13G); an embedding column 826 of the middle housing portion 82 is embedded in the assembly hole 730 of the upper surface of pushing guide wire control handle 73; the front end 8251 of the dentate convex 825 at the proximal end of the middle housing portion 82 is far away from the oblique groove convex 8331 of the lower housing portion 83; a front end 8252 of the dentate convex at the distal end of the middle housing portion 82 is in contact with or close to a right convex 8342 of the connecting portion 834 of the lower housing portion 83; at this time, the finger acts on the dentate convex 825 of the middle housing portion 82 and rotates clockwise as indicated by the arrow to drive the pushing guide wire 6 and the occluding wire 3 to move forward in an arc-shaped track.

As shown in FIG. 13G, the sectional view from another angle shows that the control handle lumen 530 of the occluding wire 3 is connected with the fluid transfer part lumen 540 in the coaxial state.

As shown in the horizontal sectional view of FIG. 13H, in the coaxial state, the control handle 73 is located at point a, the end 62 of the pushing guide wire 6 is fixed therein, and the control handle 53 is located at point c.

As shown in FIG. 13I, the middle housing portion 82 rotates clockwise as indicated by the arrow, the front end 8251 of the dentate convex 825 at the proximal end of the middle housing portion 82 contacts the oblique groove convex 8331 of the lower housing portion 83, and rotates in place; at this time, as shown in the local sectional view of FIG. 13J, the blind end 311 of the front section of the occluding wire 3 moves to the rear-end opening 202 of the venous catheter, and the front end 61 of the pushing guide wire 6 is located in the blind end 311; at this time, pushing guide wire control handle 73 moves forward to point b, and the control handle 53 moves forward to point d, as shown in the horizontal sectional view of FIG. 13K.

As shown in FIG. 13L, the upper housing portion 81 rotates clockwise as indicated by the arrow to drive the occluding wire 3 moving forward. As shown in the local sectional view of FIG. 13M, the blind end 311 of the occluding wire 3 extends from the front-end opening 201 of the venous catheter 2 to reach the occluded state, and the corrugated isolating element 5 in the accommodating groove 830 is significantly compressed. At this time, most of the isolating element 5 in the figure is located in the connecting portion lumen 8340. The pushing guide wire isolating element 7 is stretched to the maximum extent; the horizontal sectional view of FIG. 13N shows that at this time, the control handle 53 moves forward to the position of point e, while the pushing guide wire control handle 73 is still at the position of point b. This design can ensure that the pushing guide wire 6 does not enter the venous catheter lumen 20 or slightly enters the lumen, so as to ensure that the hollow front section 31 of the occluding wire 3 will not significantly increase the deflection of the venous catheter 2 in the occluded state, thus eliminating the possible additional damage to the venous wall. The accommodating groove 830 guides and limits the isolating element 5, the occluding wire 3, the pushing guide wire isolating element 7 and the pushing guide wire 6 in the whole process.

Reverse operation is to be performed for removal of the occlusion.

Embodiment 14

FIG. 14A, 14B, 14C, 14D show a venous catheter device of Embodiment 14. The biggest difference from the previous embodiments is that the solution in this embodiment can realize sensitive blood return and needle tip protection in the process of needle travel. As shown in the local sectional view of FIG. 14A, the needle tube base 16 has a lumen 160, the bottom portion 15 of the needle tube 1 is located in the needle base lumen 160, the rear end of the hard portion **25*a* of the sealer 25 participating in accommodating the needle tube 1 has a tubular extension portion 26, the extension portion lumen 260 accommodates part of the needle tube 1, the bottom part of the tubular extension portion 26 of the sealer 25 is sleeved in the needle base lumen 160, the bottom portion 15 of the needle tube 1 is sleeved with a compression spring E which can drive the needle tube 1 to move axially relative to the venous catheter base 23, one end of the compression spring E contacts the bottom of the needle base lumen 160, the other end contacts the bottom surface 261 of the tubular extension portion 26, and the right side of the tubular extension portion 26 has a local opening 262; the compression spring E extends axially to push the bottom surface 261 of the tubular extension portion 26, the sealer 25 and the venous catheter base 23, so that the front-end opening 201 of the venous catheter lumen 20 covers the sharp front end 111 of the needle tube 1**.

Figure 14A:
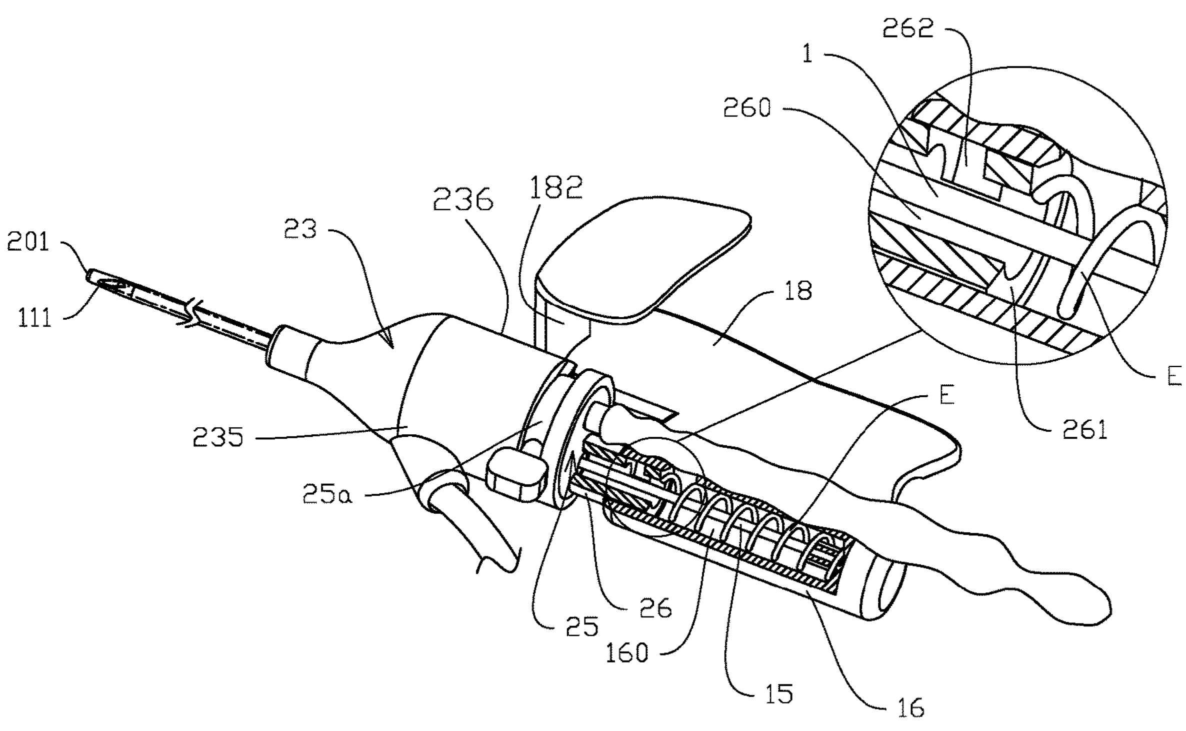
FIGS. 14A, 14B, 14C and 14D are sectional views of the occludable venous catheter device according to Embodiment 14.
Figure 14B:
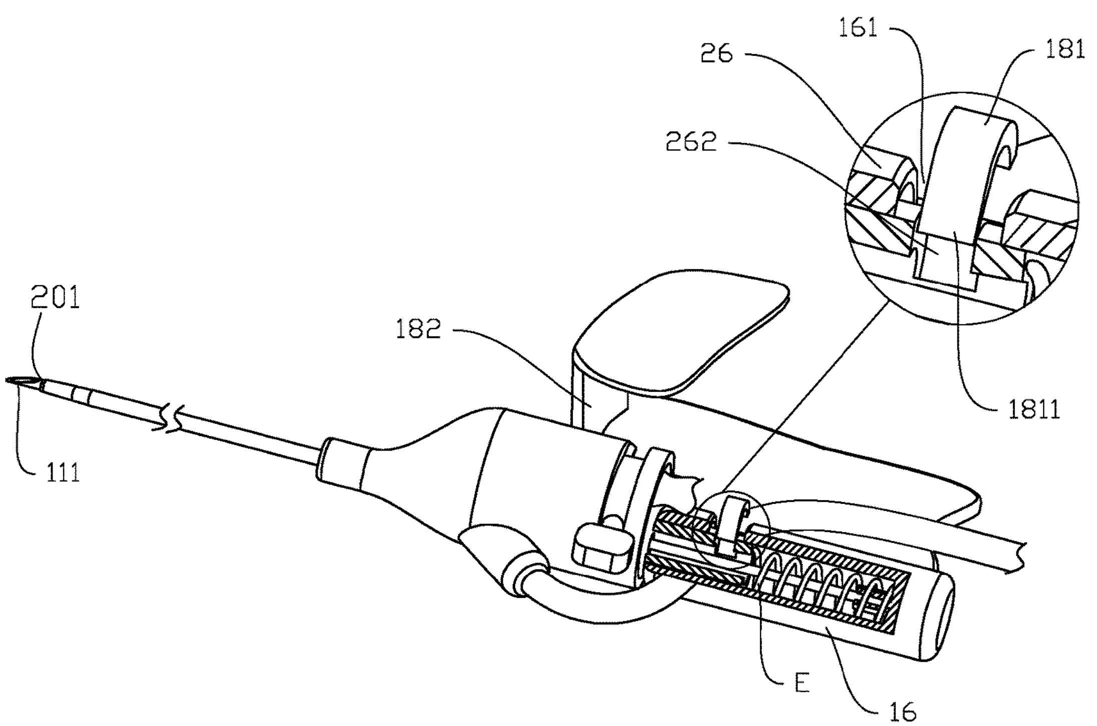

The needle tube base 16 is connected with a blade-shaped handle 18, which extends to the right side 236 of the venous catheter base 23, and the front end thereof has a bending portion 182, as shown in FIG. 14B. The handle 18 has a pressing piece 181 that bend to left with an arc-shaped horizontal section in the area corresponding to a local opening 262 of the tubular extension portion 26 of the sealer 25, and the needle tube base 16 also has a local opening 161 in the area corresponding to the local opening 262 of the tubular extension portion 26 of the sealer 25. A free section 1811 of the pressing piece 181 can be embedded into the local opening 262 of the tubular extended portion 26 of the sealer 25 through the local opening 161 of the needle tube base 16. In this state, the compression spring E is compressed, the elastic potential energy is stored, and the sharp front end 111 of the needle tube 1 extends from the front-end opening 201 of the venous catheter 2, and venipuncture can be performed.

Figure 14C:
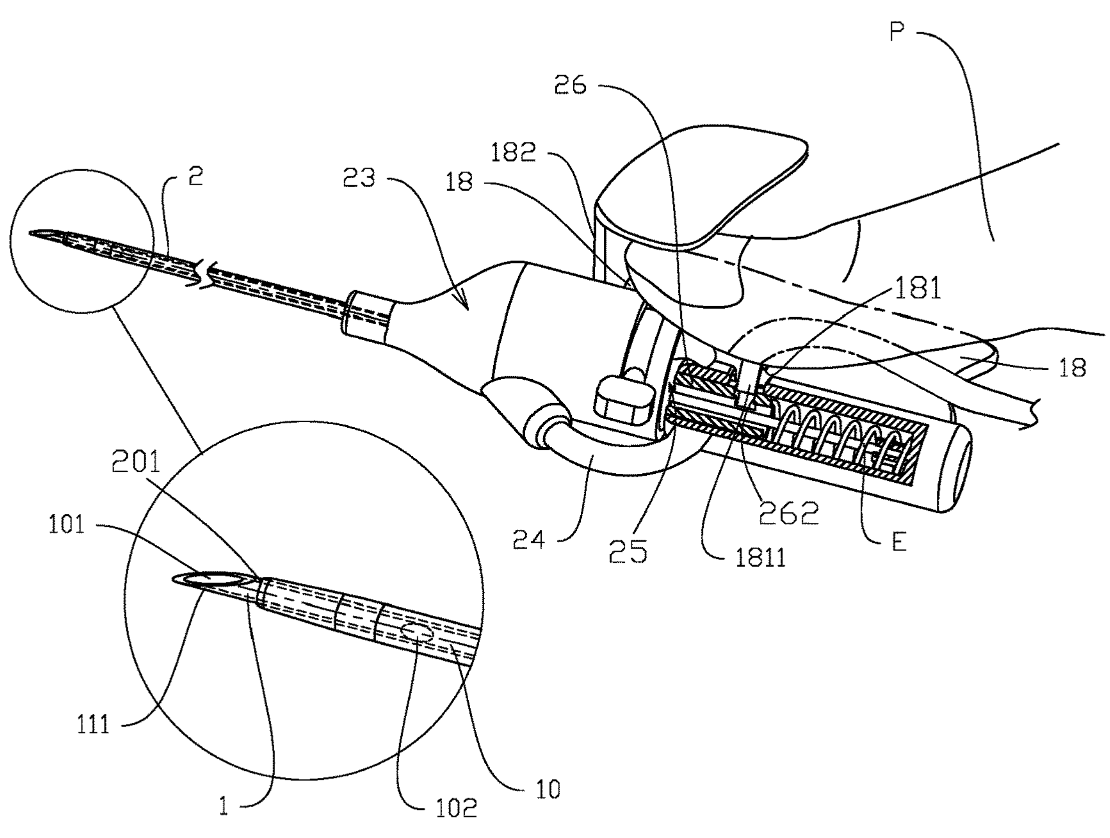

During puncture, as shown in FIG. 14C, the finger P presses the flexible medical liquid infusion connecting pipe 24 against the upper surface of handle 18 to make the infusion connecting pipe 24 locally concave and deformed (not shown). At the same time, the finger P also embeds the free section 1811 of handle pressing piece 181 into the local opening 262 of the tubular extension portion 26 of sealer 25 to prevent the tubular extension portion 26 of sealer 25 from being pushed forward by the elastic force of compression spring E. The finger P slightly releases when feeling that it has entered the venous lumen V0, the negative pressure attraction generated by the elasticity recovery at the place where the infusion connecting pipe 24 is pressed will actively inhale the venous lumen blood into the needle tube lumen 10. Through the transparent venous catheter 2, it can be timely observed at the side opening 102 of the front end of the needle tube 1 whether there is blood return. The sensitive and active blood return function is particularly important for patients with low blood pressure in the venous lumen; the finger continues releasing to allow rebounding of the pressing piece 181 when blood return is observed, the free section 1811 moves out from the local opening 262 of the tubular extension portion 26 of the sealer 25, and the elastic potential energy of the compression spring E is released to push the tubular extension portion 26 of the sealer 25, the venous catheter base 23 and the venous catheter 2 to move forward, so that the front-end opening 201 of the venous catheter lumen 20 covers the sharp front end 111 of the needle tube 1. Because the front part of finger P is placed against the front bending portion 182 of the handle 18, the handle 18 is prevented from moving backward due to stretching of the compression spring E, as shown in FIG. 14A. If the needle continues to enter the vein lumen V0, the vein wall V will not be punctured, so as to achieve safe needle entry.

Figure 14D:
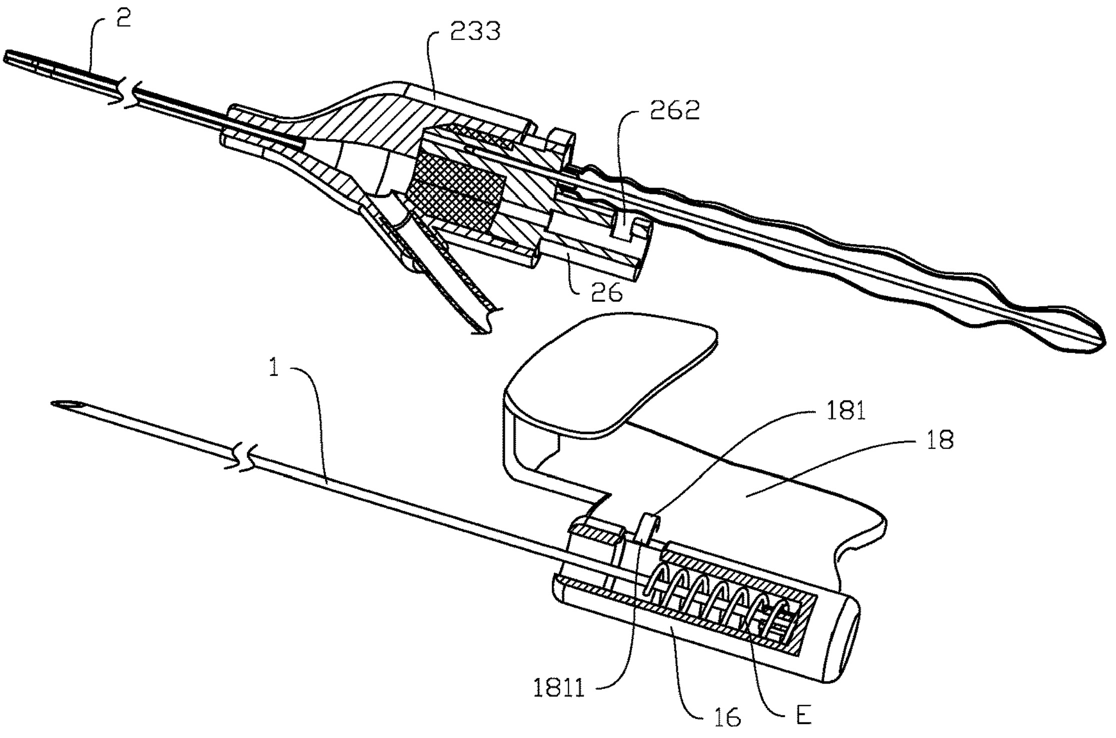

FIG. 14D shows that after successful venipuncture, the needle tube 1 is removed, the infusion of medical liquid can be started, and the occlusion of venous catheter 2 described in the previous embodiments can also be started.

The blade-shaped handle 18 connected with the needle tube base 16 can also be disposed on the upper surface 233 or the left side surface 235 of the venous catheter base 23; the free section 1811 of the pressing piece 181 on the handle 18 may not necessarily be embedded in the local opening 262 of the tubular extension portion 26 of the sealer 25, but in close contact with the outer surface of the tubular extension portion 26 without opening, by which the generated frictional resistance may also resist the elastic force of the compression spring E.

Embodiment 15

Figure 15A:
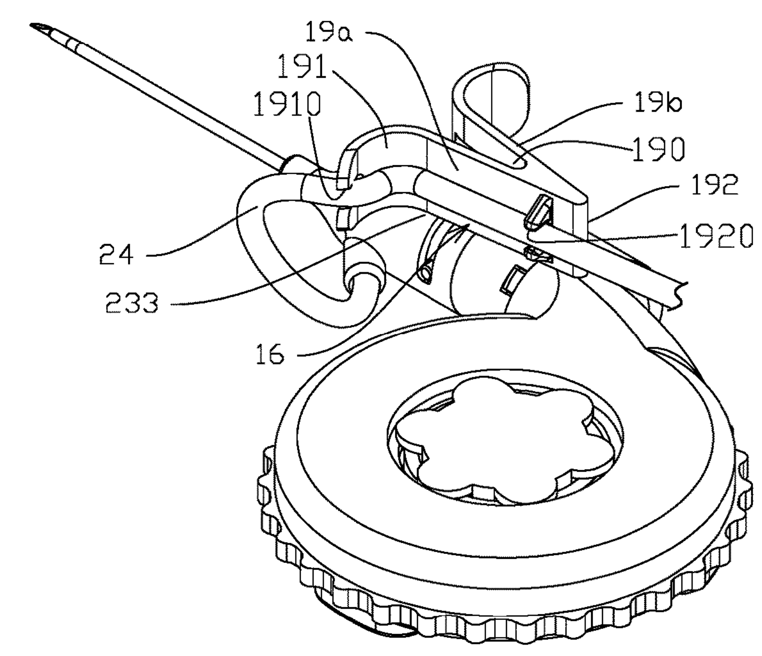
FIGS. 15A and 15B are perspective views of the occludable venous catheter device according to Embodiment 15.
Figure 15B:
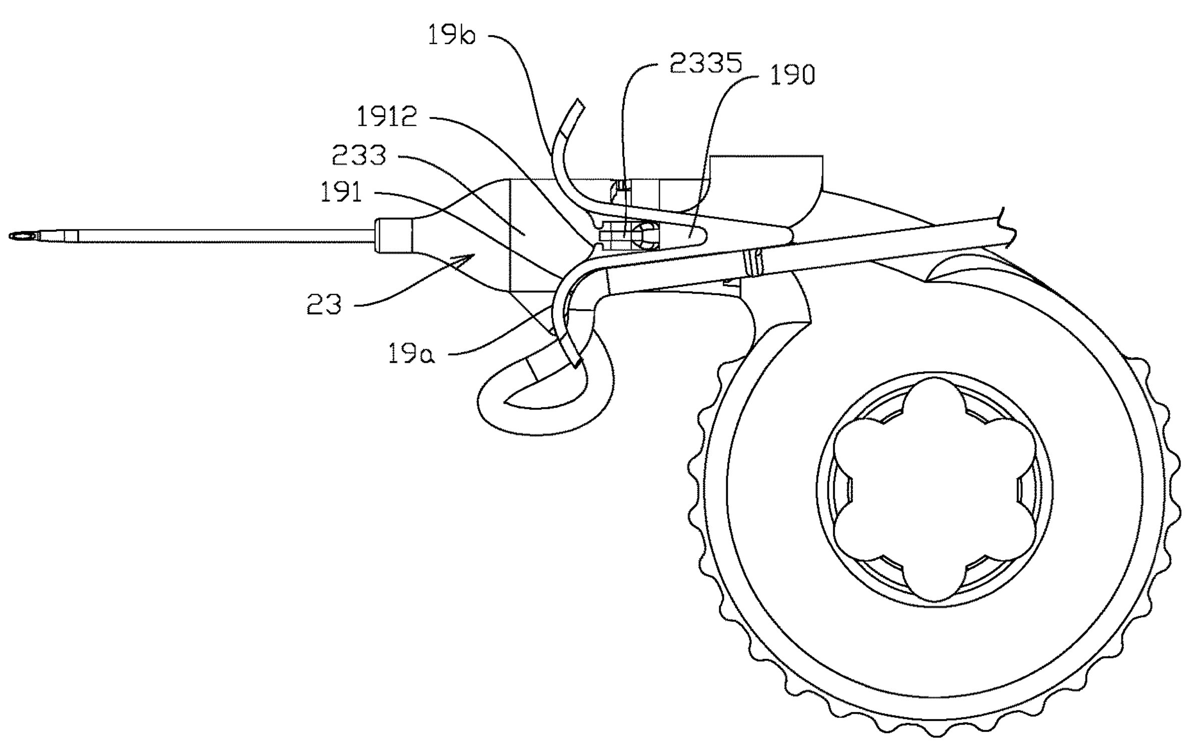

FIGS. 15A and 15B show a venous catheter device of Embodiment 15. In order to achieve better active and sensitive blood return and safe needle entry, the difference of this embodiment from Embodiment 14 is that, the occluding mechanism in Embodiment 13 is used in this embodiment, and that as for the design of the needle tube base handle as shown in FIG. 15A, the needle tube base 16 is connected with two blade-shaped handles **19*a* and 19*b* respectively with a bending front end, defined as a right handle and a left handle; the handles 19*a* and 19*b* extend upward and to the left and right at the upper surface 233 of the venous catheter base 23, and there is a clearance 190 between the two; the edge of a bending portion 191 of the left handle 19***a* has a notch 1910, the left side of a connecting portion 192 of the handles 19*a* and 19*b* has a rib-shaped notch 1920, and the notch 1910 and the rib-shaped notch 1920 can be embedded in the flexible infusion connecting pipe 24 for medical liquid infusion. As shown in FIG. 15B, the upper surface 233 of the venous catheter base 23 has a longitudinally disposed convex rib 2335 extending upward, and the convex rib 2335 is located in the clearance 190. When two fingers press 19*a* and 19*b* centripetally, the front end of the convex rib 2335 is obstructed by a convex 1912 on the inner side of the starting point of the handle bending portion 191. At this time, the venous catheter base 23 cannot move forward even if pushed by the compression spring E; when the handles 19*a* and 19*b* move to both sides under the control of fingers, the convex 1912 on the inner side of the handle bending portion 191 will release the obstruction to the convex rib 2335. At this time, if the compression spring E pushes, the venous catheter base 23 will move forward. Because the front portion of the finger P is placed against the front-end bending portion 191 of the handles 19*a* and 19*b*, the handles 19*a* and 19*b* will be prevented from moving backward due to the stretching of the compression spring E (the same as that in Embodiment 14, not shown), so that the same effect as stated in Embodiment 14 is achieved.

The invention claimed is:

1. An occludable venous catheter device, comprising:

a needle tube (1) for puncturing skin and venous wall, having a bottom portion (15), a front portion (11) and a front end (111);

a needle tube base (16) connected to the bottom portion (15) of the needle tube (1);

a venous catheter (2) having a venous catheter lumen (20), a rear-end opening (202) and a front-end opening (201);

a venous catheter base (23) connected to the rear-end opening (202) in a sealed manner, having a chamber (230);

a sealer (25) disposed on the venous catheter base (23) for sealing the chamber (230) of the venous catheter base (23);

an occluding wire (3) covered at least partially by an isolating element (5) which isolates the occluding wire (3) from the outer environment;

the needle tube (1) passing through the sealer (25), the front portion (11) of the needle tube (1) located inside the venous catheter lumen (20), and the front end (111) of the needle tube (1) passing through the front-end opening (201) and being exposed;

wherein, the venous catheter device further comprises a guide passage (40) having a straight tube portion (41) at least at the front of the guide passage (40) and a front-end opening (401) connected to the venous catheter lumen (20) directly or through the chamber (230);

the occluding wire (3) is capable of entering the venous catheter lumen (20) through the guide passage (40);

at least the straight tube portion (41) of the guide passage (40) is coaxial with the venous catheter (2) or the straight tube portion (41) is capable of moving in an externally-isolated manner to a position that a central axis (L2) of the straight tube portion (41) coincides with a central axis (L1) of the venous catheter (2);

the occluding wire (3) and the guide passage (40) reach directly inside the chamber (230) and are isolated from the outer environment;

the sealer (25) or a portion of the sealer (25) having the guide passage (40) is rotatably connected inside the venous catheter base (23), and a rotation axis (L3) of the sealer (25) is parallel to the central axis (L1) of the venous catheter (2); and the rotation axis (L3) is distinct from and equidistant between the central axis (L2) of the guide passage (40) and the central axis (L1) of the venous catheter (2).

2. The venous catheter device of claim 1, further comprising an infusion connecting pipe (24) having an infusion connecting pipe lumen (240) which is connected to the chamber (230) of the venous catheter base (23) through the sealer (25).

3. The venous catheter device of claim 1, wherein a rotation handle (255) is disposed on the sealer (25), and the venous catheter base (23) has a limiting structure and/or a guiding structure (2331) for allowing the rotation handle (255) to rotated around the venous catheter base (23).

* * * * *